(12) United States Patent
Stokes et al.

(10) Patent No.: US 9,826,965 B2
(45) Date of Patent: Nov. 28, 2017

(54) DEVICES FOR SEALING A BODY LUMEN

(71) Applicant: Ethicon LLC, Guaynabo, PR (US)

(72) Inventors: Michael J. Stokes, Cincinnati, OH (US); Chester O. Baxter, III, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 197 days.

(21) Appl. No.: 14/300,820

(22) Filed: Jun. 10, 2014

(65) Prior Publication Data
US 2015/0351730 A1 Dec. 10, 2015

(51) Int. Cl.
*A61B 17/00* (2006.01)
*A61B 17/11* (2006.01)
*A61B 17/12* (2006.01)

(52) U.S. Cl.
CPC .... *A61B 17/0057* (2013.01); *A61B 17/00491* (2013.01); *A61B 17/11* (2013.01);
(Continued)

(58) Field of Classification Search
CPC ............ A61B 17/11; A61B 17/1128; A61B 17/00491; A61B 17/07292; A61B 2017/1107; A61B 2017/1132; A61B 2017/1114; A61B 2017/00522; A61B 17/1114; A61B 2017/1125;
(Continued)

(56) References Cited

U.S. PATENT DOCUMENTS

| | | | |
|---|---|---|---|
| 5,254,113 A | | 10/1993 | Wilk |
| 5,336,221 A | * | 8/1994 | Anderson ............ A61B 18/22 606/150 |

(Continued)

FOREIGN PATENT DOCUMENTS

| | | |
|---|---|---|
| WO | 0162159 A2 | 8/2001 |
| WO | 2005074817 A1 | 8/2005 |

(Continued)

OTHER PUBLICATIONS

Chen et al. "Elastomeric Biomaterials for Tissue Engineering." Prog. Polymer. Sci. 38(2013):584-671.
(Continued)

*Primary Examiner* — Christopher L Templeton
(74) *Attorney, Agent, or Firm* — Mintz Levin Cohn Ferris Glovsky and Popeo, P.C.

(57) ABSTRACT

Various surgical kits are provided including a sealing cuff configured to be positioned around a body lumen and a sealant. In one embodiment, the sealing cuff can form an enclosed loop around an anastomosis and can define an interior chamber for receiving sealant therein. The sealing cuff can ensure that sealant remains in contact with the body lumen as the sealant cures and reinforces the anastomosis. Methods for sealing an anastomosis are also provided and include delivering sealant to the sealing cuff, inserting inflatable members so that they are positioned adjacent to the anastomosis, and delivering fluid to at least one of the inflatable members to expand an inner wall of the tubular organ. In certain aspects, gas and/or liquid can be delivered to an anastomosis, such as after the sealant has solidified, in order to test the effectiveness of the seal.

15 Claims, 15 Drawing Sheets

(52) U.S. Cl.
CPC .. *A61B 17/12045* (2013.01); *A61B 17/12109* (2013.01); *A61B 17/12136* (2013.01); *A61B 17/00234* (2013.01); *A61B 2017/00646* (2013.01); *A61B 2017/1132* (2013.01)

(58) Field of Classification Search
CPC .... A61B 2017/2926; A61B 2017/2945; A61B 17/282; A61B 17/115; A61B 17/1152; A61B 17/1155; A61B 2017/1135; A61B 2017/1139
See application file for complete search history.

(56) References Cited

U.S. PATENT DOCUMENTS

| | | | |
|---|---|---|---|
| 5,698,213 | A | 12/1997 | Jamiolkowski et al. |
| 5,700,583 | A | 12/1997 | Jamiolkowski et al. |
| 5,749,895 | A * | 5/1998 | Sawyer ............ A61B 17/00491 606/154 |
| 7,143,924 | B2 | 12/2006 | Scirica et al. |
| 7,143,925 | B2 | 12/2006 | Shelton, IV et al. |
| 7,772,352 | B2 | 8/2010 | Bezwada |
| 8,317,070 | B2 | 11/2012 | Hueil et al. |
| 8,393,514 | B2 | 3/2013 | Shelton, IV et al. |
| 8,551,058 | B2 | 10/2013 | Measamer et al. |
| D754,325 | S * | 4/2016 | Ilan .............................. D24/108 |
| 2002/0116016 | A1* | 8/2002 | Barath ................... A61B 17/11 606/153 |
| 2006/0085031 | A1* | 4/2006 | Bettuchi .......... A61B 17/00491 606/215 |
| 2006/0257458 | A1 | 11/2006 | Gorman et al. |
| 2006/0271104 | A1 | 11/2006 | Viola et al. |
| 2007/0162123 | A1 | 7/2007 | Whittaker et al. |
| 2008/0109019 | A1* | 5/2008 | Tulleken ................ A61B 17/11 606/153 |
| 2008/0114466 | A1* | 5/2008 | Shelton .................. A61B 17/11 623/23.7 |
| 2009/0234193 | A1 | 9/2009 | Weisenburgh, II et al. |
| 2009/0270686 | A1 | 10/2009 | Duke et al. |
| 2011/0082497 | A1* | 4/2011 | Deslauriers ...... A61B 17/00491 606/213 |
| 2011/0192882 | A1 | 8/2011 | Hess et al. |
| 2011/0264122 | A1* | 10/2011 | Bonino ............ A61B 17/00491 606/153 |
| 2012/0024934 | A1 | 2/2012 | Shelton, IV et al. |
| 2012/0078293 | A1* | 3/2012 | Hassidov ......... A61B 17/00491 606/213 |
| 2012/0080335 | A1 | 4/2012 | Shelton, IV et al. |
| 2012/0083835 | A1 | 4/2012 | Shelton, IV et al. |
| 2013/0112733 | A1 | 5/2013 | Aranyi et al. |
| 2013/0146642 | A1 | 6/2013 | Shelton, IV et al. |
| 2013/0153638 | A1* | 6/2013 | Carter .................. A61B 17/072 227/179.1 |
| 2013/0153641 | A1 | 6/2013 | Shelton, IV et al. |
| 2013/0161374 | A1 | 6/2013 | Swayze et al. |
| 2013/0256365 | A1 | 10/2013 | Shelton, IV et al. |
| 2013/0256372 | A1 | 10/2013 | Baxter, III et al. |
| 2013/0256376 | A1 | 10/2013 | Barton et al. |
| 2013/0256377 | A1 | 10/2013 | Schmid et al. |
| 2014/0088642 | A1* | 3/2014 | Ilan .................. A61B 17/00491 606/214 |
| 2014/0158741 | A1 | 6/2014 | Woodard, Jr. et al. |
| 2014/0188141 | A1* | 7/2014 | Ilan .................. A61B 17/00491 606/153 |
| 2015/0173756 | A1 | 6/2015 | Baxter, III et al. |
| 2015/0272575 | A1 | 10/2015 | Leimbach et al. |

FOREIGN PATENT DOCUMENTS

| | | |
|---|---|---|
| WO | 2006044799 A2 | 4/2006 |
| WO | 2014016819 A1 | 1/2014 |

OTHER PUBLICATIONS

Lim et al. "Fabrication and Evaluation of Poly(epsilon-caprolactone)/Silk Fibroin Blend Nanofibrous Scaffold." Biopolymers. 97(2012):265-275.
U.S. Appl. No. 13/763,192, filed Feb. 8, 2013.
U.S. Appl. No. 14/074,810, filed Nov. 8, 2013.
U.S. Appl. No. 14/074,884, filed Nov. 8, 2013.
U.S. Appl. No. 14/074,902, filed Nov. 8, 2013.
U.S. Appl. No. 14/075,438, filed Nov. 8, 2013.
U.S. Appl. No. 14/075,459, filed Nov. 8, 2013.
U.S. Appl. No. 14/300,793, filed Jun. 10, 2014.
U.S. Appl. No. 14/300,799, filed Jun. 10, 2014.
U.S. Appl. No. 14/300,801, filed Jun. 10, 2014.
U.S. Appl. No. 14/300,804, filed Jun. 10, 2014.
U.S. Appl. No. 14/300,807, filed Jun. 10, 2014.
U.S. Appl. No. 14/300,811, filed Jun. 10, 2014.
U.S. Appl. No. 14/300,815, filed Jun. 10, 2014.
U.S. Appl. No. 14/300,817, filed Jun. 10, 2014.
U.S. Appl. No. 14/300,819, filed Jun. 10, 2014.
U.S. Appl. No. 14/300,954, filed Jun. 10, 2014.
Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.
International Search Report and Written Opinion for Application No. PCT/US2015/032510 dated May 17, 2016.

\* cited by examiner

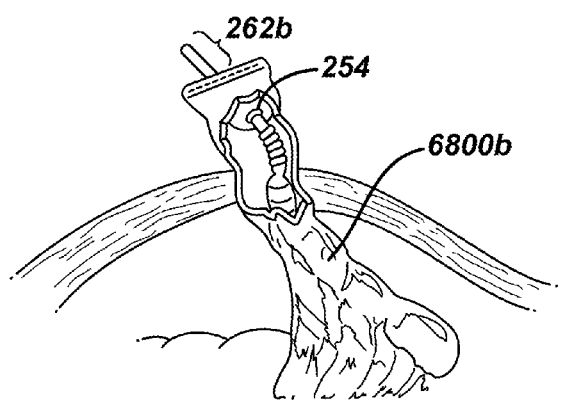
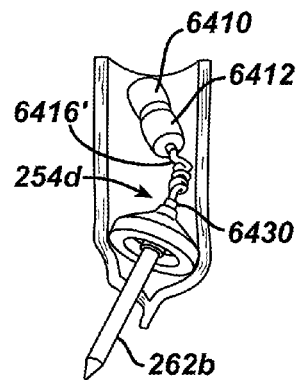
FIG. 10A  FIG. 10B
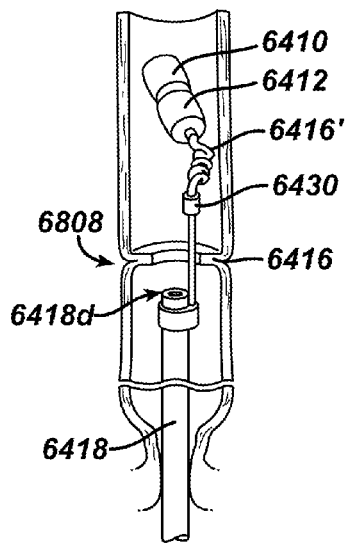
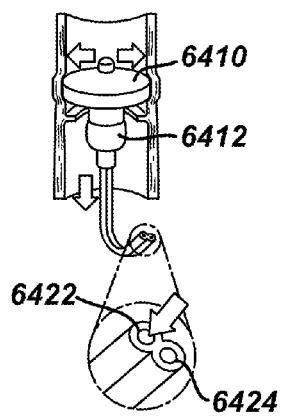
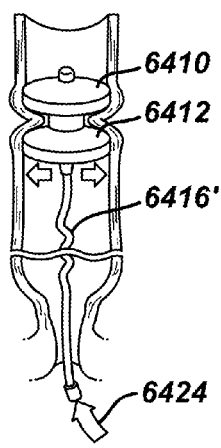
FIG. 10C  FIG. 10D  FIG. 10E

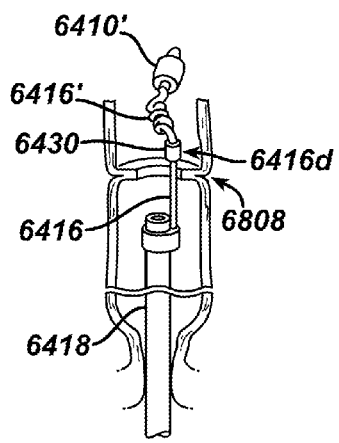 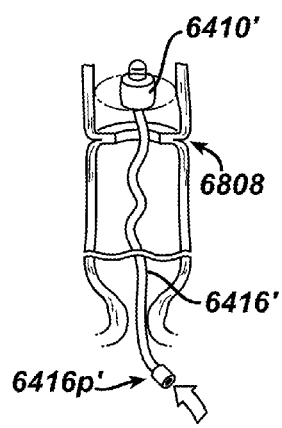 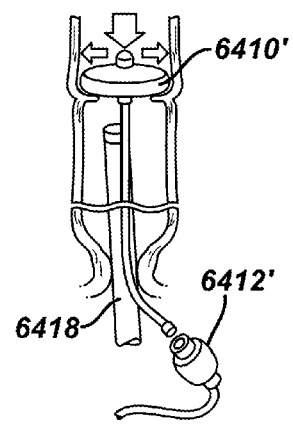
*FIG. 12A*  *FIG. 12B*  *FIG. 12C*
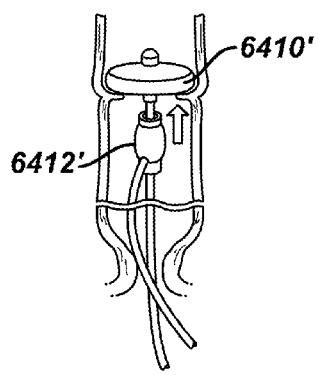 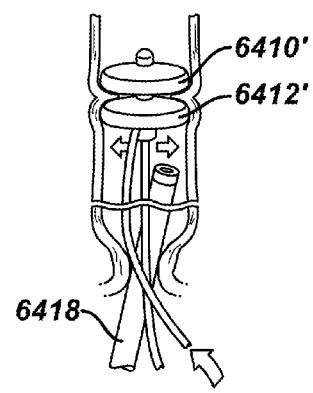
*FIG. 12D*  *FIG. 12E*

100 # DEVICES FOR SEALING A BODY LUMEN

FIELD

The subject matter disclosed herein relates to surgical methods and devices for sealing a body lumen.

BACKGROUND

Surgical staplers are used in surgical procedures to seal, divide, and/or transect tissues in the body by closing openings in tissue, blood vessels, ducts, shunts, or other objects or body parts involved in the particular procedure. The openings can be naturally occurring, such as passageways in blood vessels, airways or an internal lumen or organ like the stomach, or they can be formed by the surgeon during a surgical procedure, such as by puncturing tissue or blood vessels to form a bypass or an anastomosis, or by cutting tissue during a stapling procedure.

There are various types of staplers suited for particular surgical procedures. For example, linear staplers include a handle with an elongate shaft having a pair of opposed jaws formed on an end thereof for holding and forming staples therebetween. At least one of the opposed jaws is movable relative to the other. The staples are typically contained in a staple cartridge assembly, which can house multiple rows of staples and is often disposed in one of the two jaws for ejection of the staples to the surgical site. Circular staplers have a handle and an elongate shaft with an anvil and a cartridge assembly disposed on a distal end of the elongate shaft, the anvil axially movable relative to the cartridge assembly and configured to form staples therebetween and deploy the staples into tissue.

While surgical staplers have improved over the years, a number of problems can potentially arise. Although rare, as illustrated in FIG. 1, one problem is that leaks can occur due to staples S forming tears H when penetrating a tissue T or other object in which the staples S are disposed. Blood, air, gastrointestinal fluids, and other fluids can seep through the tears H formed by the staples S, even after the staples S are fully formed. The tissue T being treated can also become inflamed due to the manipulations and deformations that can occur during stapling. Still further, staples, as well as other objects and materials implanted during stapling procedures, generally lack the same characteristics as tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

In the particular case of stapling a colon, it is important that the staple line of the anastomosis is substantially sealed so that gastrointestinal solids and fluid remain in the organ. Leakage from the tubular body organ, e.g. a colon, can interfere with normal digestive function and can introduce bacteria into other portions of the body, causing infection. However, it can be difficult to prevent leaks in a tubular body organ for a variety of reasons. For example, it can be difficult for the tissue disposed near the staple line to withstand repeated expansion and contraction that occurs when solids and fluid passes through the colon. Additionally, it can be difficult to deliver sealant to the tubular body organ and control the position of the sealant when it is curing from a liquid state to a solidified state Accordingly, there remains a need for improved surgical methods and devices for sealing a body lumen.

SUMMARY

In one embodiment, a surgical kit is provided that includes a liquid sealant and a sealing cuff. The liquid sealant can be configured to cure into a solidified state. The sealing cuff can have a sidewall with first and second ends removably mated to one another to form an enclosed loop, and the sidewall can define an interior chamber. In use, the sealing cuff can be configured to be disposed around a body lumen such that the interior chamber is sealed between the outer wall and the body lumen to allow the liquid sealant to be received therein and to directly contact the body lumen. The surgical kit can further include a tube coupled to the sealing cuff and configured to deliver the sealant to the interior chamber of the sealing cuff.

The sealing cuff can vary in any number of ways. For example, the sidewall can be substantially hemispherical and an inner surface of the sidewall can be substantially concave. The sealing cuff can include a plurality of protrusions formed on inner surface of the sidewall for facilitating distribution of the sealant within the interior chamber. In certain aspects, the plurality of protrusions can be spaced evenly about a circumference of the sidewall. For another example, the sealing cuff can include sutures coupled to an inner surface of the sidewall. In certain aspects, the sutures can be disposed in a criss-cross pattern. The sealing cuff can further include a locking mechanism for removably mating the first and second ends.

The surgical kit can further include at least one expandable member configured to move from a compressed position to an expanded position and having a shape that substantially corresponds to a shape of the interior chamber of the sealing cuff when the at least one expandable member is in the expanded position.

The sealant can also vary in a number of ways. For example, the sealant can be selected from the group consisting of fibrin, thrombin, a hydrogel, benzocaine, cyanoacrylate, polyglycolic acid, hyaluronic acid, magnesium peroxide, hydrogen peroxide, platelet rich plasma, and combinations thereof. In certain aspects, the sealant can be configured to transition from the liquid to the solidified state after a predetermined amount of time.

A surgical device is provided that includes a sealing cuff having a ring-shaped sidewall, the sidewall defining an interior chamber configured to hold a sealant therein. The sealing cuff can include a plurality of extensions for distributing the sealant within the interior chamber, the plurality of extensions being sized and shaped such that when the sealing cuff is disposed around a tubular body organ and sealant is delivered thereto, the sealant is distributing substantially uniformly in thickness within the interior chamber of the cuff and solidifies substantially circumferentially around the organ.

The surgical device can vary in any number of ways. The sealing cuff can further include a port formed therein and configured to mate with a delivery tube for delivering a sealant to the interior chamber of the cuff. The plurality of extensions can vary in a number of ways. For example, each of the extensions can be disposed radially around the sealing cuff. For another example, the plurality of extensions can be spaced along an inner surface of the interior chamber. In certain aspects, the plurality of extensions can be substantially cylindrical-shaped.

Methods for reinforcing an anastomosis of a tubular organ are also provided and in one embodiment, the method can include forming an anastomosis in a tubular organ, applying a sealing cuff around the anastomosis, the sealing cuff including at least one strand of suture extending along an inner surface of the sealing cuff and having a woven structure for containing a sealant, and injecting a sealant into an interior chamber of the sealing cuff such that the sealant directly contacts and forms a substantial seal around the anastomosis.

The method can be performed in various ways. In certain aspects, the anastomosis can be formed in the tubular organ prior to delivering the sealant into the interior chamber of the sealing cuff. In other aspects, the anastomosis can be formed in the tubular organ after the sealant is delivered into the interior chamber of the sealing cuff. Injecting the sealant into the interior chamber of the sealing cuff can cause the sealant to solidify around the at least one strand of suture. In certain aspects, after the sealant is solidified, the sealant can be released from the interior chamber of the cuff by detaching the at least one strand of suture from the sealing cuff.

BRIEF DESCRIPTION OF THE DRAWINGS

The invention will be more fully understood from the following detailed description taken in conjunction with the accompanying drawings, in which:

FIG. 10A is a perspective, semi-transparent view of an anvil of a circular stapler positioned inside of a tubular organ;

FIG. 10B is a side, semi-transparent view of the anvil and tubular organ of FIG. 10A, the anvil having first and second expandable members coupled thereto;

FIG. 10C is a side, semi-transparent view of the tubular organ of FIG. 10B formed into an anastomosis and having the first and second expandable members coupled to a scope;

FIG. 10D is a side, semi-transparent view of the first expandable member positioned proximal to the anastomosis, in an expanded position;

FIG. 10E is a side, semi-transparent view of the first and second expandable members disposed on opposite sides of the anastomosis, in their expanded positions;

FIG. 12A is a partial cross-sectional view of an anastomosis of a tubular organ, along with a scope having a tether coupled thereto that is attached to a first expandable member;

FIG. 12B is a partial cross-sectional view of the first expandable member being positioned proximal to the anastomosis as a terminal end of the tether is positioned outside of the patient's body;

FIG. 12C is a partial cross-sectional view of the first expandable member being inflated to an expanded position and the second expandable member being positioned over the tether;

FIG. 12D is a partial cross-sectional view of the second expandable member moving toward the anastomosis in a compressed position;

FIG. 12E is a partial cross-sectional view of showing the second expandable member being inflated to an expanded position through its inflation lumen;

DETAILED DESCRIPTION

Figure 1:
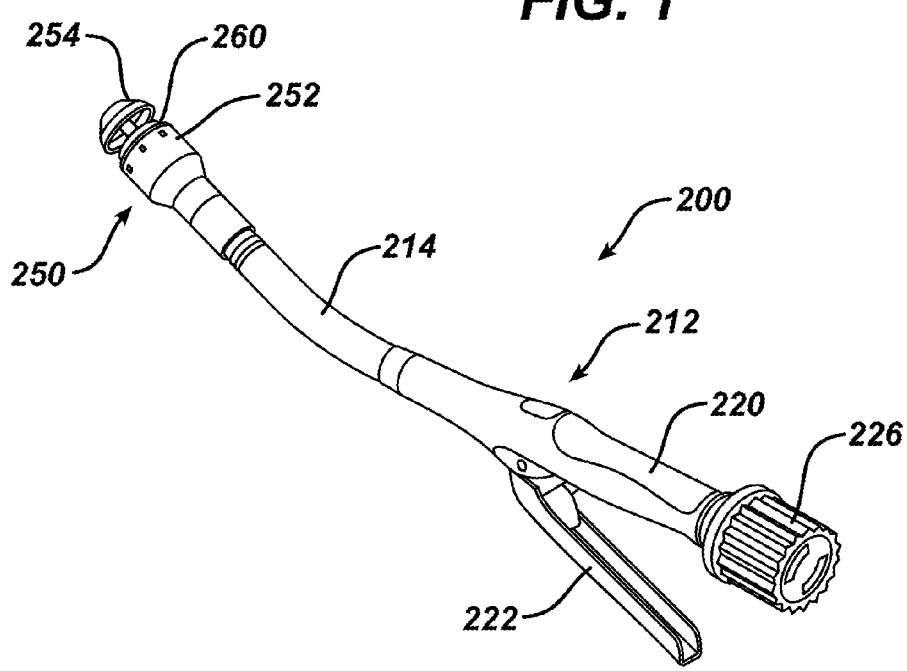
FIG. 1 is a perspective view of an exemplary circular stapler for forming an anastomosis.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of such devices and methods is defined solely by the claims. The features illustrated or described in connection with one exemplary embodiment may be combined with the features of other embodiments. Such modifications and variations are intended to be included within the scope of the devices and methods described herein. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the methods, apparatus, devices, and systems described herein.

Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary sealants and methods of sealing a tubular body organ are provided herein. In general, the sealants can facilitate sealing around a stapled body lumen, such as around a colon or around an intestinal anastomosis. A sealant can be formulated in various ways and can have various properties, but is generally provided in a first, liquid state and then cures to a second, solidified state after a predetermined amount of time. For example, the sealant can be introduced to the tubular body organ and can help reinforce a seal at the staple line of an anastomosis. When the sealant is in its liquid state, the sealant can seep into the staple line and can solidify therein, thereby facilitating a complete sealing of the tubular body organ at the staple line. The sealant can facilitate short term sealing of the tubular body organ and can be formulated so that it is absorbed into the body after the tubular body organ has healed at the anastomosis. In certain aspects, a sealing cuff is provided that can act as a mold or form for holding the sealant at the desired location, e.g. adjacent to a staple line, when the sealant is in the first, liquid state. One or more expandable members can be configured to expand the tubular body organ to further maintain contact between the sealant and the sealing cuff. In this way, the sealing cuff can be configured to hold the sealant at the desired location so that the sealant is more likely to completely seal the staple line and remain sealed as liquid and solid material passes through the tubular body organ during normal bodily functions.

The method can be performed in various ways. For example, at least one expandable member can be inserted into the tubular organ within an anastomosis. The expandable member can be inserted in a first, compressed position and can be moved to a second, expanded position to increase a diameter of a portion of the tubular organ. In general, one or more expandable members can be positioned adjacent to the staple line so that the tissue surrounding the staple line can be expanded. A sealing cuff can be positioned around an outer surface of the tubular organ and around the staple line. When the expandable member is expanded, the tissue can move toward the sealing cuff. The sealant can be predisposed within or introduced into the sealing cuff to reinforce a seal at the staple line of the anastomosis. A method for conducting a leak test of an anastomosis is also provided and can be performed before or after a sealant is applied thereto allow a surgeon to visually identify whether there are openings between the tissue and the staple line during expansion and contraction of the organ. Liquid or gas can be delivered into the organ using various techniques and visualization techniques can be used to allow a user can visually identify whether the liquid/gas is leaking out of the organ through the staple line. This can help a user determine whether sealant should be applied to reinforce the tissue during the surgical procedure, or if sealant has already been applied, whether additional sealant or other sealing techniques should be used to reinforce the seal. As described further below, the sealing cuff and expandable member(s) can be used in conjunction with the leak test, such as to reinforce the tissue after a user identifies leakage through the anastomosis.

Surgical Stapling Instrument

As will be appreciated by persons skilled in the art, various surgical staplers known in the art can be used to form an anastomosis. In general, as shown in FIG. 1, a surgical stapler 200 includes a handle assembly 212 with a shaft 214 extending distally therefrom, an end effector 250 being disposed on a distal end thereof for treating tissue. The end effector 250 can include a cartridge assembly 252 and an anvil 254, each having a tissue-contacting surface 260p, 260d that is substantially circular in shape. The cartridge assembly 252 and anvil 254 can be coupled together via a shaft 262 extending from the anvil 254 to the handle assembly 212 of the stapler 200, and manipulating an actuator 222 on the handle assembly 220 can retract and advance the shaft 262 to move the anvil 254 relative to the cartridge assembly 252. In one embodiment, the shaft 262 can be formed of first and second portions (not shown) configured to releasably couple together to allow the anvil 254 to be detached from the cartridge assembly 252, allowing greater flexibility in positioning the anvil 254 and the cartridge assembly 252 in a body. For example, the first portion of the shaft can be disposed within the cartridge assembly 252 and extend distally outside of the cartridge assembly 252, terminating in a distal mating feature. The second portion of the shaft 214 can be disposed within the anvil 254 and extend proximally outside of the cartridge assembly 252, terminating in a proximal mating feature. In use, the proximal and distal mating features can be coupled together to allow the anvil 254 and cartridge assembly 252 to move relative to one another. The anvil 254 and cartridge assembly 252 can perform various functions and can be configured to capture tissue therebetween, staple the tissue by firing of staples from a cartridge assembly 252 and/or can create an incision in the tissue. In general, the cartridge assembly 252 can house a cartridge containing the staples and can deploy staples against the anvil 254 to form a circular pattern of staples around a circumference of a tubular body organ.

The handle assembly 212 of the stapler 200 can have various actuators disposed thereon that can control movement of the stapler. For example, the handle assembly 212 can have a rotation knob 226 disposed thereon to facilitate positioning of the end effector 250 via rotation, and/or a trigger 222 for actuation of the end effector 250. Movement of the trigger 222 through a first range of motion can actuate components of a clamping system to approximate the jaws, i.e. move the anvil 254 toward the cartridge assembly 252. Movement of the trigger 222 through a second range of motion can actuate components of a firing system to cause the staples to deploy from the staple cartridge assembly 252 and/or cause advancement of a knife to sever tissue captured between the cartridge assembly 252 and the anvil 254.

The surgical stapler 200 is only one example of many different staplers that can be used in conjunction with the sealant and sealing cuffs disclosed herein. Further detail on the illustrated embodiment, as well as additional exemplary embodiments of surgical staplers, components thereof, and their related methods of use, that can be used in accordance with the present disclosure include those devices, components, and methods provided for in U.S. Publication No. 2013/0256377, U.S. Pat. No. 8,393,514, U.S. Pat. No. 8,317,070, U.S. Pat. No. 7,143,925, each of which is incorporated by reference herein in its entirety.

Sealing Cuff

Figure 2A:
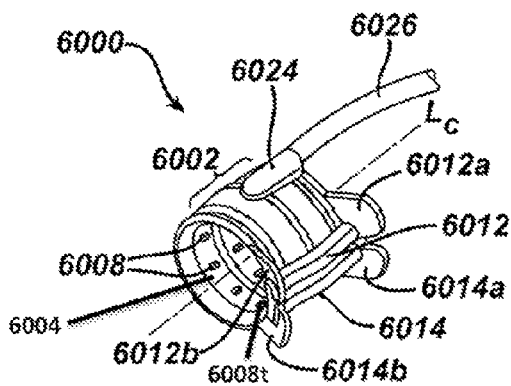
FIG. 2A is a perspective view of a sealing cuff, according to one exemplary embodiment.
Figure 2B:
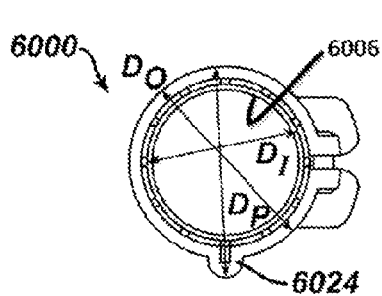
FIG. 2B is a side view of the sealing cuff of FIG. 2A.
Figure 2C:
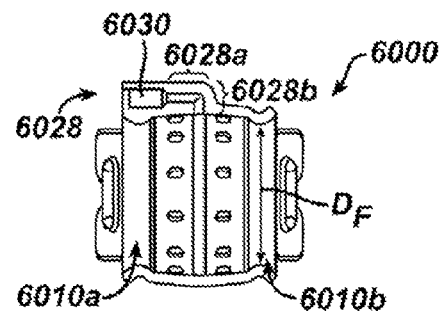
FIG. 2C is a cross-sectional view of the sealing cuff of FIG. 2A.

A sealing cuff is provided herein that can be positioned around a tubular body organ and can act as a mold for a sealant when the sealant is in the first, liquid state. The sealing cuff can have various sizes, shapes, but is generally configured to be positioned around an anastomosis of a tubular organ. In general, the sealing cuff can be formed from a spherical-shaped member with truncated proximal and distal ends. The sealing cuff can include a central portion and first and second flared portions. The central portion of the cuff can correspond to a shape of a tubular body organ, while the first and second flared portions can facilitate movement of the cuff along the tubular organ before sealant is delivered thereto. In one embodiment shown in FIGS. 2A-2C, a sealing cuff 6000 can have a substantially circular cross-sectional shape taken along a central longitudinal axis LC of the cuff 6000. The central portion 6002 of the sealing cuff 6000 can have an inner surface 6004 configured to directly contact or be positioned adjacent to an outer surface of a tubular body organ (not shown). The inner surface 6004 can define an interior chamber 6006 for receiving a sealant therein. For example, the inner surface 6004 of the sealing cuff 6000 can have a substantially concave shape that defines the interior chamber 6006. As a result, sidewall edges of the sealing cuff can contact tissue to hold a sealant within the interior chamber of the cuff. The sealing cuff 6000 can have various features for facilitating even distribution of sealant within the interior chamber 6006. For example, the sealing cuff 6000 can include any number of protrusions 6008 formed on the inner surface 6004 of the sealing cuff 6000. In general, the protrusions 6008 can be configured to directly contact an outer surface of a tubular body organ when the sealing cuff 6000 is positioned around the organ and can prevent gravity from pulling sealant toward a low portion of the sealing cuff 6000. The protrusions 6008 can be shaped in various ways, such as cylindrical, spherical, conical, etc., and can have a radial height selected so that a terminal end 6008t of the protrusion 6008 directly contacts the outer surface of the tubular body organ. The protrusions 6008 can also be spaced apart in various ways, such as around a circumference of the sealing cuff 6000 in a single row or in multiple rows, e.g. two rows, three rows, four rows, etc. The protrusions 6008 can be spaced evenly around the circumference in a single plane or can be spaced in any other pattern configured to facilitate an even distribution of sealant within the interior chamber 6006 of the sealing cuff 6000. The protrusions can have a radial height substantially equal to or larger than a radial thickness between the inner surface of the sealing cuff and the outer surface of the body lumen to help achieve a uniform thickness of sealant around the circumference of the cuff. As shown in FIG. 2C, the sealing cuff 6000 can further include first and second flared portions positioned 6010a, 6010b on either side of the central portion 6002 of the cuff 6000 and having an inner diameter DF that is greater than the inner diameter DI of the central portion 6002 of the cuff 6000. These flared portions 6010a, 6010b can facilitate sliding the cuff around a tubular body organ, as will be discussed in greater detail. By way of non-limiting example, the inner diameter DF of the flared portions can be about 95% of the inner diameter DI of the central portion of the cuff. The sealing cuff 6000 can have a relatively thin wall, for example, with a thickness in the range of about 1 to 5 mm. An inner diameter DI of the cuff can correspond to, e.g. be greater than or equal to, an outer diameter of a tubular body organ. For example, the inner diameter DI of the sealing cuff 6000 can be in the range of about 19 to 35 mm.

The sealing cuff can have variety of features that allow it to be positioned around a tubular organ and then removed from the organ. For example, the sealing cuff 6000 in FIGS. 2A-2C can be substantially ring-shaped when the cuff 6000 inserted in a patient. One or more reinforcement ribs 6012, 6014 can extend between and substantially perpendicular to the first and second flared portions 6010a, 6010b. In order to facilitate removal of the cuff 6000 from an organ, the sealing cuff 6000 can have a breakaway portion (not shown) configured to fracture or tear when a pulling force is applied to the cuff 6000. This breakaway portion can be positioned in the narrow space between the first and second reinforcement ribs 6012, 6014, as shown in FIG. 2B. As will be appreciated by persons skilled in the art, the breakaway portion can be formed from a different, weaker material than the remaining portion of the sealing cuff 6000, e.g. different from the material forming central portion 6002 of the sealing cuff 6000 and/or the reinforcement ribs 6012, 6014. The sealing cuff 6000 can further include a plurality of tabs that can be grasped by a tool to help position the sealing cuff 6000 and/or remove the sealing cuff 6000 from an organ. For example, as shown in FIG. 2A, a first tab 6012a can be formed on a first terminal end of the first reinforcement rib 6012 and a second tab 6012b can be formed on a second terminal end of the first reinforcement rib 6012. Similarly, a third tab 6014a can be formed on a first terminal end of the second reinforcement rib 6014 and a fourth tab 6014b can be formed on a second terminal end 6014b of the second reinforcement rib 6014. Each of the tabs 6012a, 6012b, 6014a, 6014b can have a substantially rectangular cross-sectional shape with a relatively thin thickness so that the tabs 6012a, 6012b, 6014a, 6014b can be grasped by one or more tools.

The sealing cuff can be configured to move in other ways and need not include a breakaway portion. For example, the sealing cuff can pivot between an open position in which first and second ends of sealing cuff are separated and a closed position in which first and second ends of sealing cuff are joined together. In this way, when the sealing cuff is in the closed position, the sealing cuff is ring-shaped and defines the interior chamber for receiving sealant. The sealing cuff can include any number of features to facilitate pivotable movement of the sealing cuff, such as a pivot-type hinge and one or more locking mechanisms configured to lock the sealing cuff in the closed position.

A sealing cuff can include one or more ports for receiving sealant therein and for directing the sealant to the interior chamber of the cuff. For example, the sealing cuff 6000 of FIG. 2A includes a port 6024 having a delivery tube 6026 coupled thereto for delivering sealant to the cuff 6000. The port 6024 can be positioned so that it extends substantially parallel to the central longitudinal axis LC of the sealing cuff 6000 so as to minimize a diameter DP of the sealing cuff 6000 at the port 624. As shown in FIG. 2C, the port 6024 can include a passageway 6028 extending into the inner surface 6004 of the cuff 6000, the passageway 6028 having a mating feature 6030 configured to mate with the delivery tube 6026. The delivery tube 6026 can be configured to couple to the mating feature 6030 in various ways, such as via a press-fit or a snap-fit, so that the delivery tube 6026 can be removed and cleaned or replaced after a single use. The passageway 6028 can be shaped in various ways, but in the illustrated embodiment includes a first portion 6028a that is perpendicular to a second portion 6028b for receiving fluid from the port, the second portion 6028b directing the fluid substantially toward a central inner diameter of the sealing cuff and thus, toward a staple line of an anastomosis. As will be appreciated by persons skilled in the art, while the sealing cuff is shown with only one port, the cuff can include any number of ports for delivering sealant to the cuff.

Figure 3:
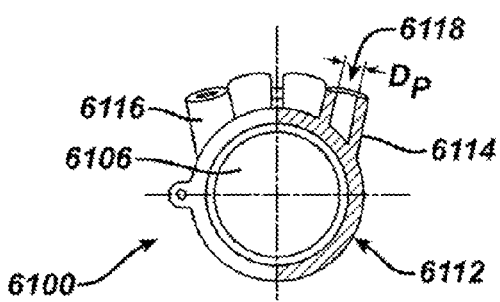
FIG. 3 is another embodiment of a sealing cuff having one or more extension ports that facilitate positioning the cuff around a body lumen.

The sealing cuff can have other features that facilitate positioning of the sealing cuff around a tubular body organ. As shown in FIG. 3, a sealing cuff 6100 can have one or more extension ports 6114, 6116 formed in an outer surface 6112. One or more of the extension ports 6114, 6116 can have an inner diameter DP sized and shaped to receive a grasping tool therein. The extension ports can have various features. As shown, the extension port 6114 can have an inner lumen 6118 that determinates on the outer surface 6112 of the sealing cuff 6100 so as to not interfere with the interior chamber 6106 of the cuff 6100. In another embodiment, the inner lumen 6118 of the extension port 6114 can be in communication with the interior chamber 6106 of the cuff such that fluid can be delivered into the interior chamber 6106 therethrough, such as through a tube (not shown) extending between the inner lumen 6118 and an outer. Any number of the extension ports can have an inner lumen configured to deliver fluid to the interior chamber 6106. The inner lumen 6118 can be substantially perpendicular to the outer surface 6112 of the sealing cuff 6000 or can be disposed at other angles relative to the outer surface 6112 of the cuff 6000. For example, as shown in FIG. 3, the sealing cuff 6100 can include the first and second extension ports 6114, 6116, the first extension port 6114 being positioned about 90 degrees relative to the second extension port 6116. In another embodiment (not shown), any number of extension ports can include features for angularly positioning the extension port relative to the outer surface of the cuff, such as a ball and socket joint. The extension ports can include locking mechanisms configured to lock the port at a desired position. As will be appreciated by a person skilled in the art, the sealing cuff 6100 can include any number of extension ports positioned at any number of locations around the sealing cuff selected so as to not substantially interfere with delivery of the cuff 6100 into a patient's body. The inner lumen 6118 can be cylindrical in shape and the inner diameter DP can be in the range of about 19 to 35 mm. The second extension port 6116 can include an inner lumen 6120 being sized and shaped substantially the same as the inner lumen 6118, or the inner lumen 6120 can have a different size and shape. A sealing cuff can include features that facilitate a user locating a position of the cuff when the cuff is in a patient. For example, the cuff and/or the graspers can be configured to emit light.

Figure 4A:
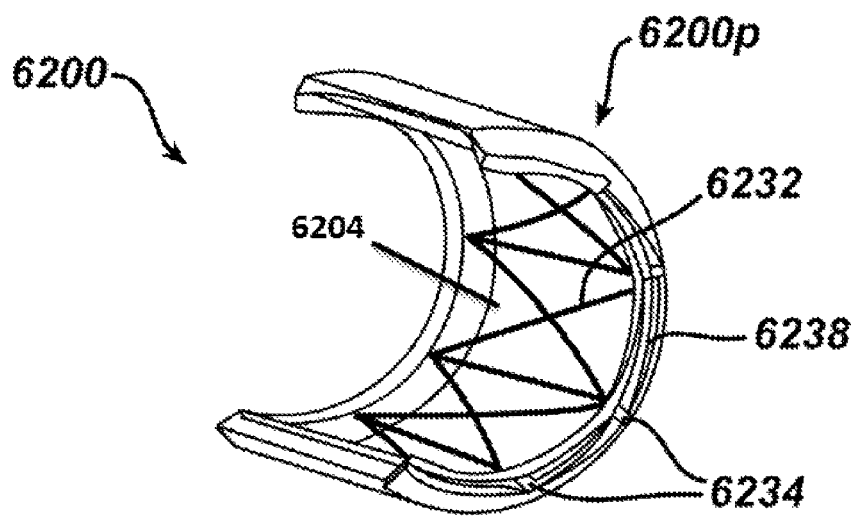
FIG. 4A is a partial, cross-sectional view of a sealing cuff having suture woven across an inner surface thereof for contacting a sealant.
Figure 4B:
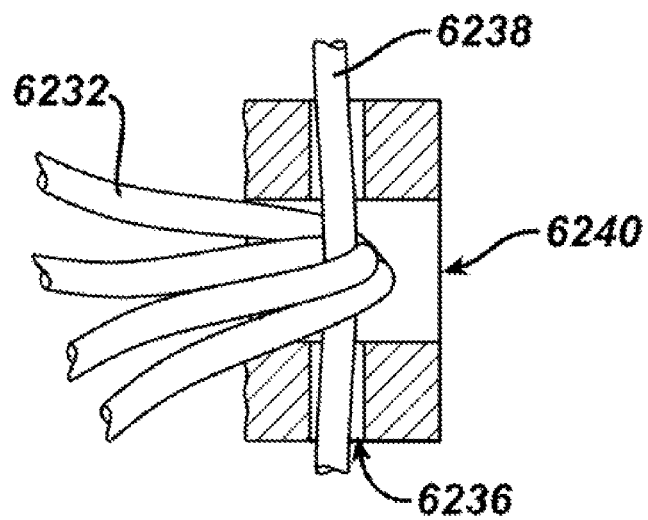
FIG. 4B is partial, side view of the sealing cuff of FIG. 4A showing a passageway formed in a wall of the cuff and having suture extending therethrough.

A sealing cuff can include other features that help hold the sealant in a desired position between the tubular body organ and the inner surface of the sealing cuff. For example, FIG. 4A illustrates a perspective, partial cross-sectional view of a sealing cuff 6200 having suture 6232 woven across an inner surface 6204 of the sealing cuff 6200. The strand of suture 6232 can be provided in a criss-crossed pattern forming intersecting triangles across the inner surface 6204 of the cuff. In another embodiment (not shown), the strand of suture 6232 can include multiple strands of suture that can be woven in various patterns across the inner surface 6204 of the cuff 6200. In general, this suture 6232 can be used to hold the sealant away from the inner surface 6204 of the sealing cuff 6200 to prevent sealant from solidifying thereon and can therefore facilitate removal of the cuff 6200 from a patient's body. The suture 6232 can be attached to the sealing cuff 6200 in various ways. For example, a plurality of attachment points 6234 can be formed on a proximal end 6200p of the cuff 6200 and spaced equally about the circumference of the proximal end 6200p of the cuff 6200. As shown in FIG. 4B, a passageway 6236 can be formed around the circumference of the proximal end 6200p of the cuff 6200 and can have an elongate member 6238, e.g. a second strand of suture, extending therethrough. The passageway 6236 can further include a plurality of radial openings formed therein, each radial opening 6240 being substantially perpendicular to the passageway 6236, as shown in FIG. 4B. Each radial opening 6240 can allow the first strand of suture 6232 to pass therethrough from the inner surface 6204 of the cuff 6200, around the second strand of suture 6238, and back through the radial opening 6240 toward the inner surface 6204 of the cuff 6200, as shown in FIG. 4B. In use, the second strand of suture 6238 can be cut to release the first strand of suture 6232 from the inner surface 6204 of the cuff.

A sealing cuff according to any of the exemplary embodiments can be formed from various materials. Preferably, the sealing cuff is formed from a substantially rigid material so that it is configured to withstand the forces applied to the cuff sealant is injected through the delivery tube and into an anastomosis. A sealing cuff can be formed into a single, unitary structure, such as via injection molding, or into multiple pieces joined together using any known fixation techniques.

Sealants

A sealant can have various formulations and differing viscosity and curing behavior. Generally, a sealant can be made from a biocompatible and bioabsorbable material that can be configured to transition from a first, liquid state to a second, solidified state via a curing process, such as a polymerization reaction. The first state can be a softened state, e.g., a fluid, a gel, a foam, etc. and the second state can be a hardened state, e.g., a solid, a rigid member, etc. When the sealant is in the first, softened state, the sealant can flow through the delivery tube and into the sealing cuff, as described in greater detail below. The sealant can transition from the first, softened state to the second, solidified state after a predetermined amount of time. In certain aspects, the sealant can be formed from biologic material. In some embodiments, the sealant can assist in wound healing by releasing various chemical compounds, during and/or after curing of the sealant in a patient's body. By way of non-limiting example, the sealant can be configured to release a therapeutic drug, such as fibrin, thrombin, etc. over time to aid the tissue in healing near the location of the sealant in a body. In one embodiment, a fibrin sealant can include two reactive components combined immediately prior to delivery into a patient, such as Thrombin and a biologically active component (BAC2), Fibrinogen and Factor XIII. In certain aspects, the components can be provided in a 5:1 volumetric ratio of BAC2 to Thrombin. While the resulting sealant can have different viscosity and curing behavior depending on its formulation, this exemplary formulation of sealant can have a viscosity in the range of about 1 cp to 90 cp after the components have been mixed and the polymerization reaction has started, and the sealant can cure to a solidified state in about 3 minutes.

Figure 5A:
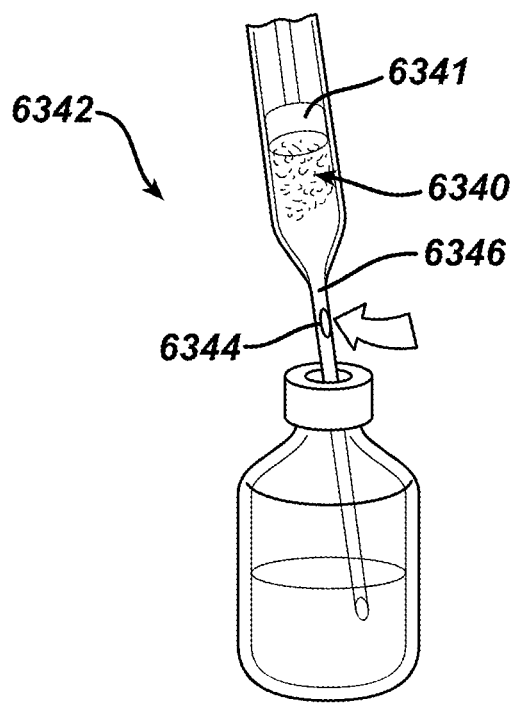
FIG. 5A is an exemplary embodiment of a foamed sealant.
Figure 5B:
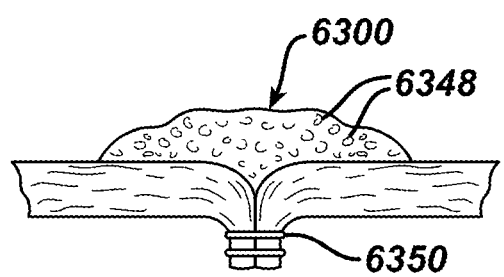
FIG. 5B is a side view of the foamed sealant of FIG. 5A penetrating into an anastomosis.

FIG. 5A illustrates a first component 6340 of a sealant 6300 positioned in an injection syringe 6342. As shown, the syringe can include a plunger 6341 for drawing the component 6340 therein. The syringe 6342 can be configured to introduce gas, e.g. air, into the component 6340 through various techniques. For example, an opening 6344 can be formed in a needle 6346 of the injection syringe 6342 so that air can be introduced into the component 6340 as it is drawn into the syringe 6342. This first component 6340 can be mixed with one or more additional components (not shown) immediately prior to or during injection into a patient, and these additional components can also have gas introduced therein. The presence of gas in one or more of the components of the sealant 6300 can form air pockets/closed cells 6348 as the sealant 6300 has solidified into a staple line 6350, as shown in FIG. 5B, resulting in a sealant 6300 that has increased flexibility in its solidified form than if the sealant 6300 lacked these air pockets/closed-cells 6348. This can allow the sealant 6300 to move more radially and longitudinally, in coordination with a movement of a tubular body organ, as the organ radially expands, contracts, and/or twists during normal bodily function. Further, this preparation technique can decrease an amount of sealant 6300 that is applied to a sealing cuff because the gas can form the closed-cells 6348 in the sealant 6300 that increase the overall volume for a given mass of sealant 6300. The presence of these closed-cells 6348 can act as a visual indicator to a user regarding the location and/or thickness of the sealant 6300.

Expandable Devices

An expandable device can be used in conjunction with a sealing cuff to hold the sealant in a desired position as the sealant cures from the liquid state to the solidified state. In general, the expandable devices provided herein can be positioned inside of a tubular body organ in a compressed position and can move to an expanded position in which the devices expand against an inner surface of the tubular body organ. This can force an outer surface of the tubular organ toward the inner surface of sealing cuff and can help hold the sealant in this position to achieve a complete seal around the anastomosis. An expandable device can have various sizes, shapes, and configurations. In some embodiments, an expandable device can include first and second expandable members so that the first expandable member can be positioned on a first side of anastomosis and the second expandable member can be positioned on second side of the anastomosis. In certain aspects, the expandable device can be expanded/inflated by delivering liquid or gas to the expandable members. In one embodiment shown in FIG. 6A, an expandable device 6400 can include first and second expandable members 6410, 6412, i.e. inflatable balloons, coupled to an elongate member 6416, such as a cylindrical rod, via a coupling mechanism 6417. The elongate member 6416 can be configured to mate with a distal end 6418*d* of a scoping device 6418, as shown, to allow a user to visualize the expandable members 6410, 6412 when the expandable device 6400 is positioned inside of a tubular body organ (not shown). The first and second expandable members 6410, 6412 can be fixedly coupled to the elongate member 6416 and spaced apart along an axial length of the elongate member 6416. The first and second expandable members 6410, 6412 can be sealed around the elongate member 6416 using any attachment mechanism known in the art, such as an adhesive. As a result, the elongate member 6416 can extend through a central longitudinal axis of each of the first and second expandable members 6410, 6412 without interfering with the expansion and compression of the expandable members 6410, 6412. As will be appreciated by a person skilled in the art, the elongate member 6416 can be made from various materials and can be flexible or semi-flexible so as to allow the elongate member to navigate a tortuous tubular body organ.

Figure 6A:
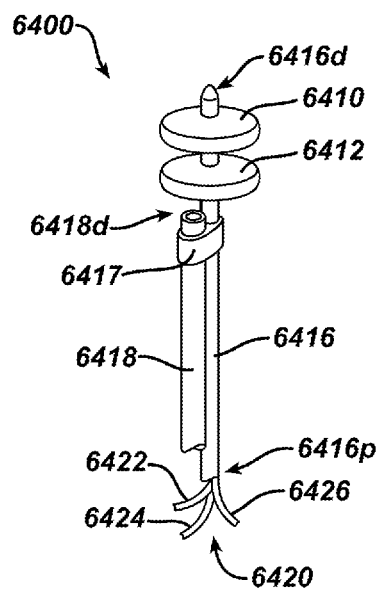
FIG. 6A is a side view of an expandable device including first and second expandable members.

The device can include various features for delivering fluid, e.g. liquid or gas, to the expandable members. As shown in FIG. 6A, the elongate member 6416 can have proximal and distal terminal ends 6416*p*, 6416*d*, and an inner lumen extending 6420 therethrough from the proximal terminal end 6416*p* of the elongate member 6416 and terminating proximal to the distal terminal end 6416*d*. The inner lumen 6420 of the elongate member 6416 can have one or more inflation lumens disposed therein for delivering fluid, e.g. liquid or gas such as saline, oxygen, carbon dioxide, etc., to one or both of the expandable members. For example, the device of FIG. 6A includes first and second inflation lumens 6422, 6424. The first inflation lumen 6422 can be configured to deliver fluid therethrough and into a first exit port (not shown) formed in the elongate member 6416, the first expandable member 6410 being disposed around the first exit port. Similarly, the second inflation lumen 6424 can be configured to deliver fluid therethrough and into a second exit port (not shown) formed in the elongate member 6416, the second expandable member 6412 being disposed around the second exit port. Each of the first and second inflation lumens 6422, 6424 can be coupled to first and second fluid sources (not shown) that can allow for selective inflation of the expandable members 6410, 6412, e.g. simultaneous inflation of the first and second expandable members 6410, 6412 or sequential inflation of the expandable members 6410, 6412 in any order. As will be appreciated by a person skilled in the art, the expandable device can have any number of inflation lumens, such as one inflation lumen in fluid communication with first and second expandable members. The expandable devices can include other features for facilitating moving the expandable members from a compressed position to an expanded position by inflating and deflating the expandable members. For example, the expandable members can include one or more valves (not shown) positioned in any of their respective inflation lumens. In certain aspects, the valves can be configured to close when the expandable member achieves a certain inflation volume to prevent liquid or gas from flowing out of the expandable members. After a procedure is performed, the valves can be opened to allow the expandable members to deflate to the compressed position to facilitate removal of the device from the patient's body.

The expandable members can have various sizes and shapes in the expanded and compressed positions. When the expandable members of FIG. 6A are in an expanded position, the expandable members 6410, 6412 can be substantially disc-shaped. The expandable members can have any size and shape configured to expand a tubular body organ, such as spherical, tubular, etc. In general, each of the expandable members can have a maximum diameter in the expanded position that is greater than an inner diameter of the tubular body organ in its resting state, such as in the range of about 110 to 115% greater than the inner diameter of the tubular body organ. As explained in further detail below, this can facilitate positioning of the sealant between an outer surface of the tubular body organ and an inner surface of the sealing cuff. The expandable members can be formed from various materials that can be inflated, such as rubber, silicone, PET, and Teflon.

Figure 6B:
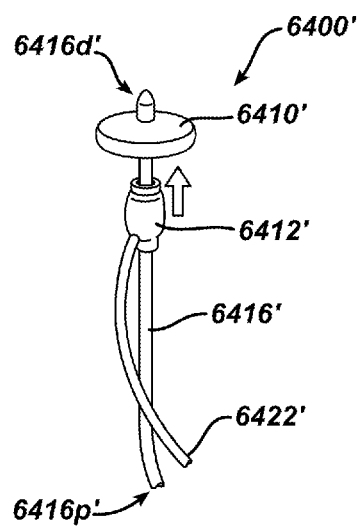
FIG. 6B is a side view of another embodiment of an expandable device having first and second expandable members.

FIG. 6B illustrates another embodiment of an expandable device having a first expandable member 6410', e.g. a first inflatable balloon, fixedly coupled to a flexible tether 6416'. A second expandable member 6412', e.g. a second inflatable balloon, can be positioned over a proximal terminal end 6416p' of a tether 6416' and can slide along an axial length of the tether 6416' in a compressed position so as to allow a user to selectively position the second expandable member 6412' relative to the first expandable member 6410'. The second expandable member 6412' can include an inflation lumen 6422' that can be integrally formed thereon or the inflation lumen 6422' can consist of a tube removably attachable to the second expandable member 6412'. As in the previous embodiment, an inflation source (not shown) can be coupled to the inflation lumen 6422'. The proximal terminal end 6416p' of the tether 6416' can also be coupled to an inflation source (not shown) while a distal terminal end 6416d' of the tether 6416' can be inserted into the tubular body organ with the first expandable member 6410' fixedly coupled thereto. In certain aspects, the distal terminal end 6416d' of the tether 6416' can be attached to an anvil of a circular stapler to allow the expandable device 6400' to be positioned inside of the tubular body organ as the anastomosis is being formed, as will be described in greater detail below. The tether 6416' can have anti-tangle features, such as being biased to a coiled position, and can be formed from a flexible material configured to navigate a tortuous tubular body organ. The tether 6416' can include a location device (not shown) such as a magnet, disposed thereon and positioned proximal to the second expandable member 6412', the location device allowing a surgeon to determine a location of the tether 6416' relative to an anastomosis.

Figure 6C:
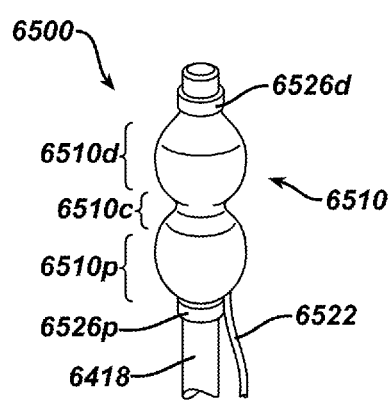
FIG. 6C is a side view of an expandable device having a single expandable member.
Figure 6D:
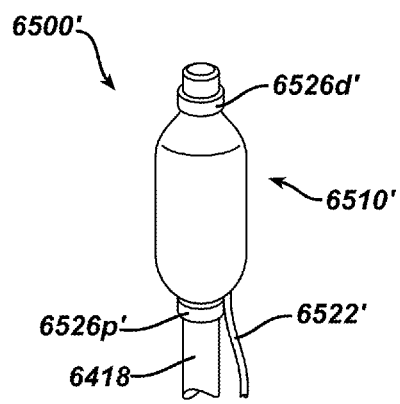
FIG. 6D is a side view of another embodiment of an expandable device having a single expandable member.
Figure 7:
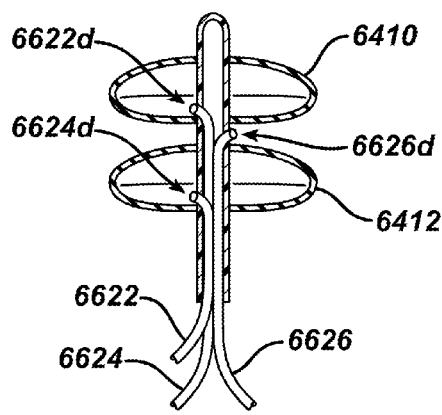
FIG. 7 is a side view of an expandable device having a lumen for delivering fluid to a space between first and second expandable members.

An expandable device can vary in any number of ways and can include a single expandable member rather than a plurality of expandable members, as shown in FIGS. 6C and 6D. In the illustrated embodiments, expandable devices 6500, 6500' can perform many of the functions of the previous expandable devices 6400, 6400' using different features. For example, expandable members 6510, 6510' are a single balloon fixedly coupled to an elongate member, such as the scope 6418 at proximal fixation points 6526p, 6526p' and distal fixation points 6528p, 6528p'. Each expandable member 6510, 6510' includes a single inflation lumen 6522, 6522' that can extend along an outer surface 6418, 6418' of the scope 6418. Alternatively, the expandable member can have an inflation lumen extending through the scope 6418 rather than along an outer surface of the elongate member. The expandable members 6510, 6510' can be shaped in various ways. For example, FIG. 6C illustrates the expandable member 6510 having proximal and distal expandable portions 6510p, 6510d that form a substantially dumbbell-shape when the expandable member 6510 is in the expanded position and having a nonexpandable central portion 6510c. FIG. 6D illustrates an expandable member 6510' having a substantially cylindrical shape when it is in the expanded position. As in the previous embodiments, a maximum diameter of each of the expandable members 6510, 6510' can be selected so that the maximum diameter is greater than an inner diameter of the tubular body organ in its resting state, that is, before the expandable members 6510, 6510' are positioned therein in the expanded position. In another embodiment shown in FIG. 7, the expandable device 6600 can include the first and second expandable members 6410, 6412, and can include first and second inflation lumens 6622, 6624 terminating in distal ends 6622d, 6624d delivered to direct fluid to the first expandable member 6410 and the second expandable member 6412, respectively. The expandable device 660 can further include a third inflation lumen 6626 having a distal end 6626d configured to deliver liquid or gas to a central portion of the device, i.e. to the space in between the first and second expandable members 6410, 6412. As will be described in greater detail below, this lumen 6626 can deliver liquid or gas to the inner wall of the anastomosis to allow a user to test leakage therefrom.

As will be appreciated by persons skilled in the art, various inflation fluids (liquid and/or gas) can be delivered to the expandable member(s), such as air, carbon dioxide, saline, water. Additionally, the inflation fluid can be colored, such as by adding methylene blue to the inflation fluid prior to injection, and can be any biocompatible contrast material known in the art to facilitate visualization of the surgical procedure.

Figure 8A:
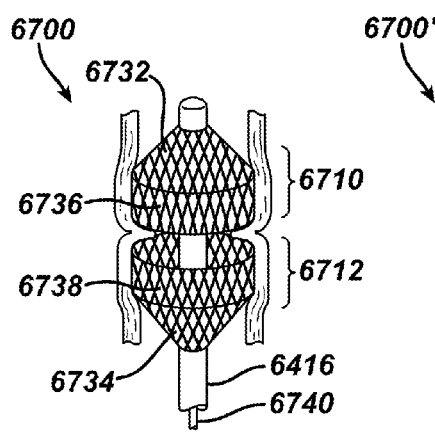
FIG. 8A is a side view of one embodiment of a stent having first and second expandable portions.
Figure 8B:
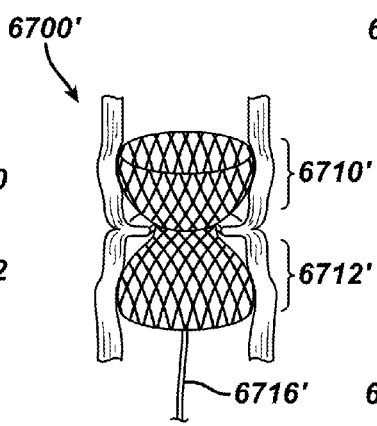
FIG. 8B is a side view of another embodiment of a stent having first and second expandable portions.
Figure 8C:
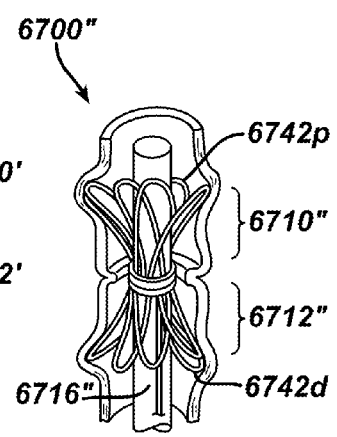
FIG. 8C is a side view of yet another embodiment of a stent having first and second expandable portions.

In other embodiments, the expandable devices can be configured to move to an expanded position without the use of liquid and inflation lumens. For example, FIGS. 8A-8C, illustrate various embodiments of stents in their expanded positions. In general, the stents can be configured to move between a compressed position and an expanded position, but can generally be biased to the expanded position. To facilitate delivery of the stent into a tubular body organ, the expandable stents can be positioned within an elongate sheath (not shown) that holds the stent in the compressed condition and can be removed once the stent is in a desired position relative to an anastomosis. As in the previous devices, the expandable stents can have various sizes, shapes, and configurations in the expanded position. For example, a stent 6700 of FIG. 8A has first and second expandable members 6710, 6712, each having a frustoconical shaped terminal portion 6732, 6734 and a central cylindrical portion 6736, 6738 configured to contact an inner wall of a tubular body organ adjacent to the anastomosis when the stent 6700 is in the expanded position. The stent 6700 can be coupled to an elongate member 6716 or rod having an actuator 6740 extending through the elongate member 6716. The actuator 6740 can be configured to be pulled proximally relative to the elongate member 6716 to deploy the expandable members 6710, 6712 to the expanded position of FIG. 8A. A stent 6700' of FIG. 8B can include first and second expandable portions 6710', 6712' being substantially funnel shaped and having a smaller diameter at a central portion 6736' thereof than at terminal ends 6732', 6734', the terminal ends 6732', 6734' being configured to contact an inner wall of the tubular body organ at a distance from the anastomosis. The expandable portions 6710', 6712' can be coupled to a flexible body, such as a tether 6716 that can have one or more location features (not shown) disposed thereon. A stent 6700" of FIG. 8C can include elongate bundles of wire 6742 extending along a longitudinal axis of the body organ and coupled to an elongate member 6716", the bundles of wire 6742 defining a first expandable portion 6710 and second expandable portion 6712. The proximal and distal ends 6742p, 6742d of the loops can be configured to expand against an inner wall of the tubular body organ while central portions of the loops have a same diameter in the expanded and compressed positions, i.e. have a smaller diameter than the tubular body organ at the anastomosis. As will be appreciated by persons skilled in the art, the expandable stents can be formed from various materials, such as Nitinol, metal wire, plastics, etc. While the expandable stents shown in FIGS. 8A-8C all include central portions having a maximum diameter less than a diameter of the organ at the anastomosis, the stents can include expandable central portions. The stents can vary in any number of ways and can have any combination of features, such as being coupled to a scope rather than an elongate member.

An expandable device can include features that facilitate a user locating a position of the device when it is positioned in a patient. For example, the expandable device can be configured to emit light, such as by being formed from a material that can emit light.

Delivery of Cuff to an Organ

A surgical procedure can be performed on a patient and can include removing a section of a tubular body organ that has an obstruction or tumor therein. This procedure can include, by way of non-limiting example, a lower anterior resection (LAR) of a rectum. Similarly, although the procedure is illustrated with respect to a tubular body organ, i.e. a rectum, another tubular anatomical structure, can be similarly treated such as entero-entero anastomosis of an intestine, uretero-uretero anastomosis of a kidney duct, esophagogastric anastomosis in the thorax or neck, aorto-iliac anastomosis, etc. After the section of the tubular body organ is removed, the procedure can include reattaching two sections of the tubular, e.g. performing a lumen-to-lumen anastomosis, such as using a circular surgical stapler. As will be appreciated by persons skilled in the art, the procedure can be an open surgical procedure, but is preferably a minimally invasive, laparoscopic and endoscopic surgical procedure in which multiple incisions are formed in a patient, the stomach cavity is insufflated with gas, and one or more trocars extend into the incisions and define a working channel for instruments to be inserted therethrough. A scope can be inserted through one of the incisions to allow a surgeon to visualize the surgical site. Alternatively or additionally, a scope can be inserted through a patient's body, i.e. through an anus to facilitate visualization of the surgical site. As described in greater detail below, various devices can be delivered endoscopically to the surgical site, including the expandable devices and the circular surgical stapler.

FIGS. 9A-9E illustrate an exemplary embodiment of a surgical procedure for stapling and sealing a tubular body organ using the sealing cuff. Although the procedure is illustrated with respect to the sealing cuff 6000 of FIGS. 2A-2C and the surgical stapler 200 of FIG. 1, the sealing cuff 6000 can include any combination of features described herein. Although the procedure is illustrated with respect to stapling, a tubular body organ can be sealed as discussed herein in conjunction with a type of fastener other than staples, e.g., clips, sutures, etc. While the surgical procedure is shown without an expandable device positioned inside of the tubular body organ, any of the devices herein can be used to expand the organ and force the outer surface of the organ toward the inner surface of the cuff to hold the sealant therebetween.

Figure 9A:
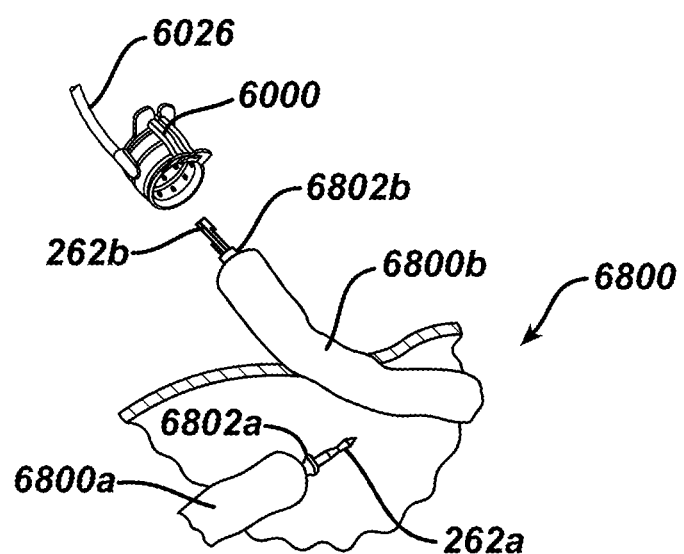
FIG. 9A is a perspective view of the sealing cuff of FIG. 2A being positioned over a first section of a tubular body organ.
Figure 9B:
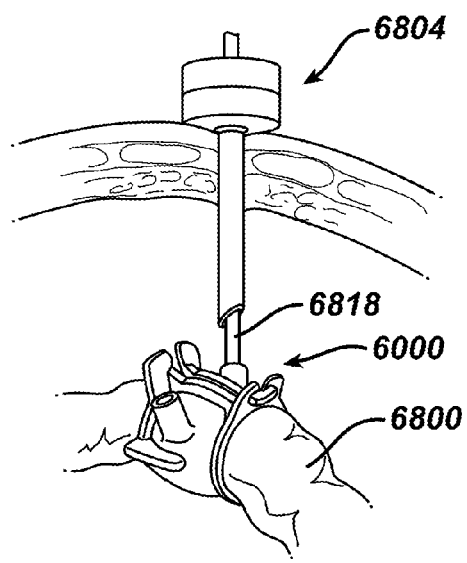
FIG. 9B is a perspective view of a trocar having a tool extending therethrough and into a positioning port formed on the sealing cuff.

FIG. 9A illustrates first and second sections 6800a, 6800b of a tubular body organ 6800 after a portion of the organ 6800 has been removed and prior to the first and second sections 6800a, 6800b being joined in an anastomosis. The first section 6800a of the tubular body organ 6800 includes the cartridge assembly (not shown) of the surgical stapler 200 positioned therein and having a first shaft portion 262a extending therefrom. As shown in FIG. 9B, the cartridge assembly can be held within the first section 6800a of the organ 6800a via one or more strands of suture 6802a. The second section 6800b of the tubular body organ 6800 includes the anvil (not shown) of the surgical stapler 200 positioned therein and having the second shaft portion 262b extending therefrom. The anvil can also be held within the second section 6800b of the organ via one or more strands of suture 6802b. Prior to joining the two sections 6800a, 6800b, the sealing cuff 6000 can be introduced onto the tubular body organ 6800 by sliding the cuff 6000 over the second shaft portion 262b and the second section 6800b of the tubular body organ.

Figure 9C:
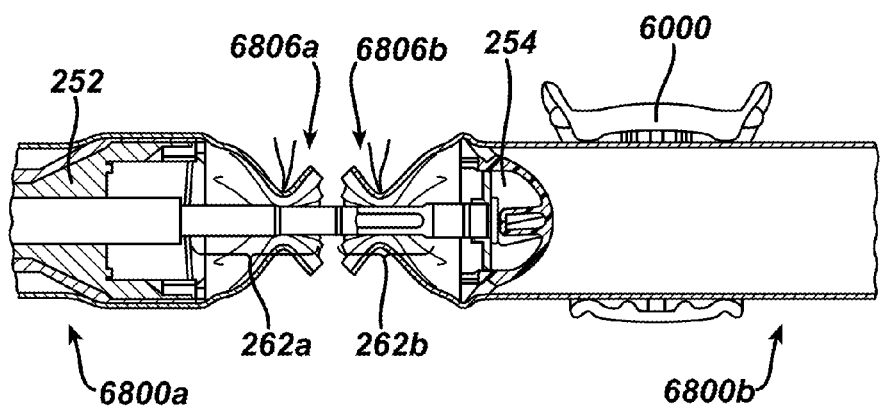
FIG. 9C is a cross-sectional view of the organ of FIG. 9A showing an anvil and cartridge assembly of a surgical stapler, the anvil positioned inside of the first section of the tubular organ and the cartridge assembly positioned inside of the second section of the tubular organ.
Figure 9D:
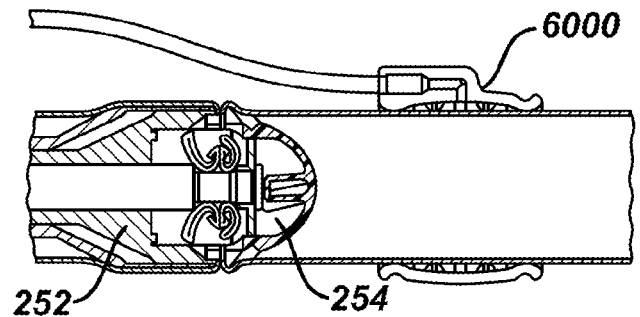
FIG. 9D is a cross-sectional view of the stapler and tubular organ of FIG. 9A, the anvil moved toward the cartridge assembly and deploying staples to form the anastomosis as the sealing cuff is positioned away from the anastomosis.

With the sealing cuff 6000 positioned on the second section 6800b of the tubular body organ 6800, the sealing cuff 6000 can optionally be held in position by inserting a first grasper tool 6818 directly through a first incision in a patient (without a trocar) or through a trocar 6804 and into a first extension port 6114 formed on the sealing cuff 6000, as shown in FIG. 9B. Optionally, a second grasper tool (not shown) can be inserted directly through a second incision in a patient (without a trocar) through a second trocar (not shown) and into the second extension port 6116. The grasper tools can be manipulated to move the sealing cuff 6000 axially along the tubular body organ 6800 and/or can rotate the sealing cuff 6000 relative to the organ 6800. In certain aspects, when the extension ports include a joint that allows angle(s) of the extension ports to be adjusted relative to an outer surface of the cuff, the grasper tools can be used to change an angle of one or more of the ports relative to the outer surface of the cuff, and each of the ports can be locked in an angulated position when a desired angle is achieved. With the sealing cuff 6000 positioned away from terminal ends 6806*a*, 6806*b* of the first and second sections 6800*a*, 6800*b* of the tubular organ 6800, the anvil 254 and the cartridge assembly 252 can be joined together, capturing tissue therebetween to begin forming an anastomosis. As shown in FIG. 9C, the first and second sections 6800*a*, 6800*b* of the tubular organ 6800 can be moved toward one another and the first and section portions 262*a*, 262*b* of the shaft 262 can then be coupled together to prepare the surgical stapler 200 to form an anastomosis. As shown, the anvil 254 and the cartridge assembly 252 of the stapler 200 can then be separated at a distance. The actuator (not shown) on the stapler 200 can be manipulated by a user, and this can retract the anvil 254 toward the cartridge assembly 252 until the anvil 254 and cartridge assembly 252 capture a portion of the tubular body organ 6800 therebetween, as shown in FIG. 9D. With the anvil 254 and cartridge assembly 252 positioned adjacent to one another, the device 200 can fire staples from the cartridge assembly 252 in a circular pattern around a circumference of the tubular body organ 6800, forming an anastomosis 6808. After the anastomosis 6808 is formed, the surgical stapler 200 can be removed from the patient, such as by retracting the stapler 200 proximally and out of the rectum of the patient.

Figure 9E:
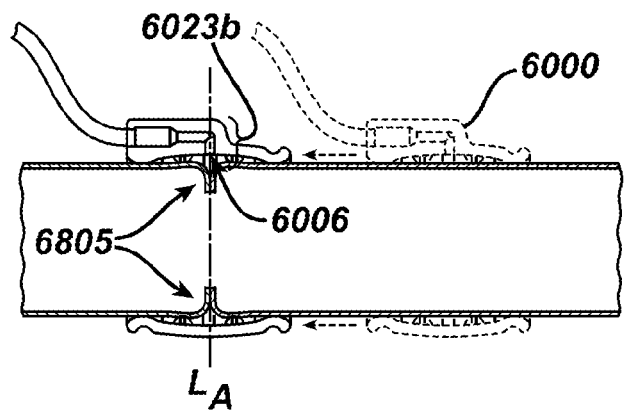
FIG. 9E is a cross-sectional view of the sealing cuff of FIG. 9A illustrating the cuff's direction of movement along the tubular organ and toward the anastomosis.
Figure 9F:
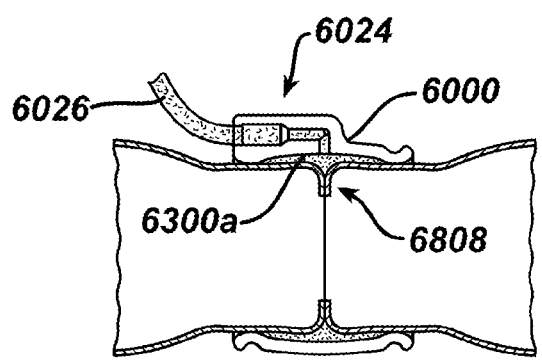
FIG. 9F is a cross-sectional view of the sealing cuff of FIG. 9A showing sealant being delivered to the sealing cuff and into the anastomosis.
Figure 9G:
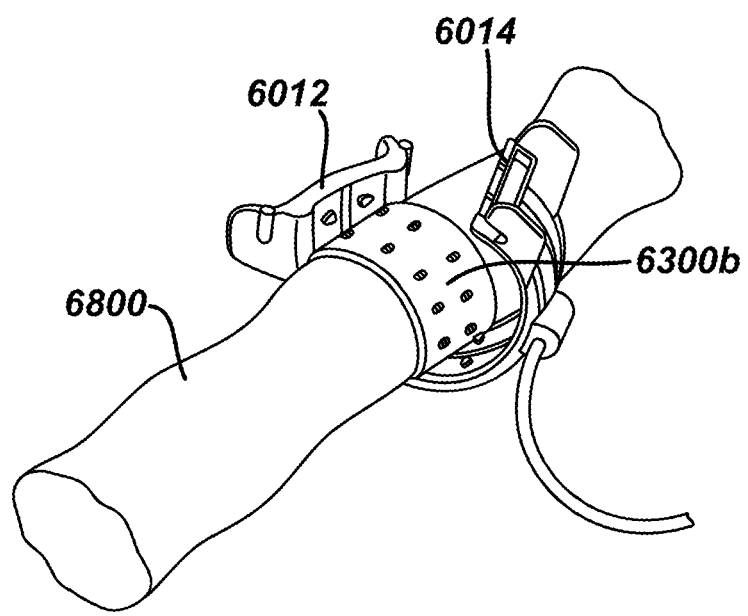
FIG. 9G is a perspective view of the sealing cuff of FIG. 9A being removed from the tubular organ after the sealant has cured around the anastomosis.

The sealing cuff 6000 can be positioned over the anastomosis 6808 in various ways and can be moved toward the anastomosis 6808, such as by sliding the cuff 6000 relative thereto, as shown in FIG. 9E. The interior chamber 6006 of the sealing cuff 6000 can be positioned over the anastomosis 6808 so that the sealing cuff 6000 can direct the sealant 6300 toward the anastomosis 6808. For example, the sealing cuff 6000 can be substantially centered over the anastomosis 6808, that is, the second portion 6028*b* of the passageway 6028 can be aligned with a central longitudinal axis LA of the anastomosis 6808 to facilitate delivery of the sealant 6300 thereto. If the sealing cuff is configured to emit light, as previously mentioned, a user can visually monitor a position of the cuff based in part on a location of the emitted light. As shown in FIG. 9F, with the sealing cuff 6000 in the desired position, the sealant 6300 can be introduced into the delivery tube 6026 when the sealant 6300 is in a liquid state and can pass through the port 6024 and into the interior chamber 6306 of the cuff 6000. The sealant 6300 can seep into the staple line of the anastomosis 6808 and can solidify therein so as to prevent leaks. As will be appreciated by persons skilled in the art, a sufficient volume of the sealant 6300 can be delivered into the interior chamber 6306 so that the sealant 6300 is positioned 360 degrees around the anastomosis 6808. The protrusions 6008 formed on the inner surface 6004 of the sealing cuff 6000 can help distribute the sealant 6300 evenly across the anastomosis 6808 and can ensure that gravity does not pull the sealant 6300 toward a portion of the sealing cuff 6000 closest to the ground. The sealing cuff 6000 can remain positioned around the anastomosis 6808 until the sealant 6300 transitions from the liquid state to the solidified state for a predetermined amount of time, at least as long as the curing time of the sealant 6300. In certain aspects, the sealing cuff 6000 can be rotated around the body lumen as the sealant 6300 is curing from the liquid to the solidified state to facilitate uniform coverage of the sealant 6300 around the anastomosis. After the sealant 6300 has cured and is in its solidified state, one or more grasping tools (not shown) can contact and grasp the sealing cuff 6000 at various locations, such as along the tabs 61012*a*, 6012*b*, 6014*a*, 6014*b* or in the extension ports 6114, 6116. The grasping tools can be used to pull apart the sealing cuff 6000 and remove the breakaway sections so that the first reinforcement rib 6012 is detached from the second reinforcement rib 6014, the sealing cuff 6000 having a C-shaped profile, as in FIG. 9G. If the cuff includes suture woven on an inner surface thereof, as in the cuff 6200 previously described, the second strand of suture 6236 can be cut to release the first strand of suture 6232 from the inner surface 6204 of the cuff 6000, thereby releasing the solidified sealant 6300 from the cuff 6000. The sealing cuff 6000 can be removed from the tubular body organ 6800 and withdrawn from the patient's body, leaving a substantially ring-shaped structure of solidified sealant 6300*b* around the anastomosis 6808. The sealant 6300*b* can be absorbed into the body after a predetermined amount of time, such as after two weeks. Preferably, this time is selected so that the tubular body organ 6800 is substantially healed at the anastomosis 6808.

Delivery of Expandable Devices to an Organ

Figure 11A:
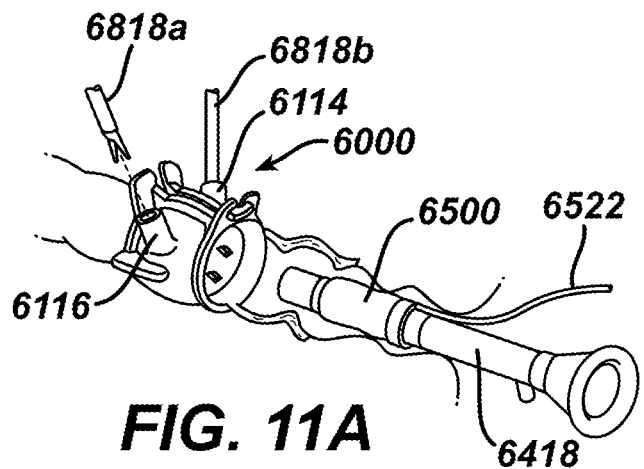
FIG. 11A is a perspective view of an expandable member disposed on a scope, the scope extending through an anus and moving toward the sealing cuff.
Figure 11B:
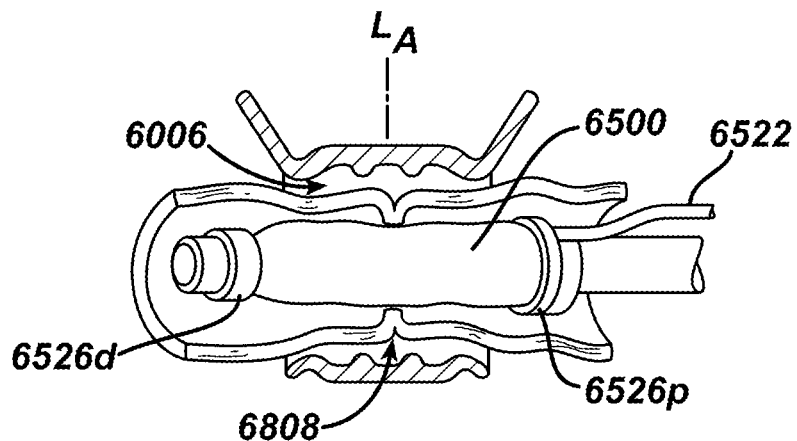
FIG. 11B is a partial cross-sectional view of the tubular organ having the scope of FIG. 11A extending therethrough, the expandable member being in a first, compressed position adjacent to the anastomosis and to the sealing cuff.
Figure 11C:
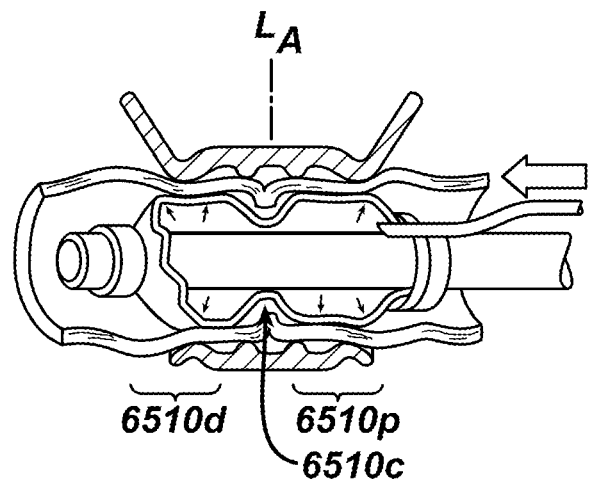
FIG. 11C is a partial cross-sectional view of the tubular organ of FIG. 11B showing the expandable member in a second, expanded position.

While the surgical procedure of FIGS. 9A-9G includes formation of the anastomosis and positioning of the sealing cuff around an anastomosis, the expandable devices disclosed herein can be used in conjunction with the sealing cuff to hold the sealant between the outer surface of the organ and the inner surface of the cuff. An expandable device can be delivered to the anastomosis in various ways, such as via the circular surgical stapler or a scope. For example, as shown in FIG. 10A, the anvil 254 of a surgical stapler 200 can be used to facilitate positioning of the expandable members 6410, 6412 inside of the tubular body organ 6800 prior to an anastomosis being formed. A tether 6416' and two expandable members 6410, 6412 can be coupled to a distal terminal end 254*d* of the anvil 254, as shown in FIG. 10B. The tether 6416' can be in a coiled position to prevent the tether 6416' from tangling around structures in the tubular body organ 6800. The tether 6416' can optionally include a location device 6430, such as a magnet, configured to allow a surgeon to visually monitor a position of the tether 6416' relative to the anastomosis. After the surgical stapler 200 fires the staples and forms the anastomosis 6808, the proximal end 6416*p*' of the tether 6416' can be detached from the anvil 254 and pulled proximally through the tubular body organ 6800 until the proximal end 6416*p*' is positioned outside of a patient's body. Alternatively, as shown in FIG. 10C, the tether 6416' and the expandable members 6410, 6412 can be coupled to the distal terminal end 6418*d* of the scoping device 6417 via the elongate member 6416 or rod. The scope 6418, elongate member 6416, and the expandable members 6410, 6412 can be inserted trans-anally through the tubular body 6800 and after a user confirms a positioning of the expandable members 6410, 6412 near the anastomosis 6800, the tether 6416' can be detached from the scoping device 6418. Any of the expandable devices/expandable members can be configured to emit light, and a user can include locate a position of the expandable device/expandable members relative to the anastomosis based in part on a location of the emitted light. The tether 6416' can be pulled proximally until the proximal end 6416*p*' of the tether 6416' is positioned outside of a patient's body. In both of these embodiments, a surgeon can position the first expandable member 6410 on a first side of the anastomosis 6808, i.e. distal to the anastomosis 6808, while the surgeon can position a second expandable member 6412 on a second side of the anastomosis 6808, i.e. proximal to the anastomosis 6808. With the expandable members 6410, 6412 so positioned, the proximal end 6416p' of the tether 6416' can be coupled to one or more inflation sources (not shown) and can deliver gas or liquid to the expandable members 6410, 6412. For example, a first inflation source (not shown) can be fluidly coupled to a first inflation lumen 6422 and can inflate the first expandable member 6410 to the expanded position, as shown in FIG. 10D. After the first expandable member 6410 is in the expanded position, a second inflation source (not shown) can be coupled to a second inflation lumen 6424 to inflate the second expandable member 6412 to the expanded position, as shown in FIG. 10E. The order of the steps can vary in any number of ways, for example, the first expandable member 6410 can be inflated at the same time as the second expandable member 6412 is inflated or the expandable members 6410, 6412 can be inflated sequentially, and this can be repeated any number of times until a desired amount of force is exerted on the tubular body organ 6800. In another embodiment shown in FIGS. 11A-11B, a scope such as a sigmoidoscope can be inserted trans-anally into the tubular body organ and can have the single expandable member 6500 positioned thereon. When the scope is inserted in the anus, as shown in FIG. 11A, the expandable member 6500 can be in the compressed position. More specifically, a surgeon can insert the expandable member 6500 into the anus of a patient so that the first coupling member 6526d is positioned on a first side of the anastomosis 6808, i.e. distal to the anastomosis 6808, and so that the second coupling member 6526p is positioned on a second side of the anastomosis 6808, i.e. proximal to the anastomosis 6808. The central portion 6510c of the expandable member 6500 can be axially aligned with a central portion of the sealing cuff 6000, as shown in FIG. 11B. Further, the sealing cuff 6000 can be substantially centered over the anastomosis 6808, that is, the second portion of the passageway of the cuff 6000 can be aligned with a central longitudinal axis LA of the anastomosis 6808 to facilitate delivery of the sealant 6300 to the interior chamber 6006 of the cuff 6000 and to the anastomosis 6808. A surgeon can confirm a positioning of these devices using visualization techniques known in the art. The central portion 6510c of the expandable member 6500 can be positioned adjacent to the anastomosis 6800. As in the other devices, the expandable member 6500 and sealing cuff 6000 can be positioned so that the cuff 6000 is substantially centered over the anastomosis 6808. As shown in FIG. 11C, as gas or fluid is delivered to the expandable member 6500 through the inflation lumen 6522, the first and second expandable portions 6510p, 6510d exert a force against an inner surface of the tubular body organ 6800 and increase an outer diameter of the tubular body organ 6800. This forces the outer surface of the tubular body organ 6800 toward the inner surface 6004 of the sealing cuff 6000. As will be appreciated by a person skilled in the art, the fluid can be delivered to the expandable member 6500 until a desired volume or pressure is achieved. After the sealant has substantially cured to its solidified state, the expandable member 6500 can be moved to the compressed position by releasing the fluid therefrom, and then retracted proximally and removed from the patient's body.

Any of the expandable devices disclosed herein can be positioned proximate to the anastomosis and can move from a compressed position to an expanded position to increase an outer diameter of portions of the tubular body organ adjacent to or surrounding the anastomosis. This includes the expandable devices and the expandable stents previously described. For another example, the expandable device 6400' of FIG. 6B can be used to increase an outer diameter of the tubular body organ 6800 adjacent to or surrounding the anastomosis 6808. In this embodiment, a surgeon can selectively position the second expandable member 6412' relative to the first expandable member 6410'. More specifically, a surgeon can position the first expandable member 6410' on the first side, i.e. distal to the anastomosis 6808 and the location of the expandable member 6410' can be monitored using the scope 6418, as shown in FIG. 12A. Alternatively or additionally, a surgeon can monitor the location of the expandable member 6410' using known imaging techniques to identify the location device 6430, e.g. magnet, coupled to the proximal end 6416p' of the tether 6416' and to the distal end 6416d of the elongate member 6416. A surgeon can detach the tether 6416' from the elongate member 6416 using various techniques, such as by inserting a grasper tool (not shown) into the tubular body organ 6808 and severing the tether 6416', and the scope 6418 can be retracted proximally until it is positioned outside of the patient, as in FIG. 12B. An inflation source (not shown) can be coupled to the proximal end 6416p' of the tether 6416' and can deliver liquid or gas to expand the expandable member 6410'. As shown in FIG. 12C, the scope 6418 can be inserted into the tubular body organ 6800 and can monitor a degree of inflation and positioning of the first expandable member 6410' relative to the anastomosis 6808. The second expandable member 6412', e.g. a second inflatable balloon, can be positioned over the proximal terminal end 6416p' of the tether 6416' when the proximal terminal end 6416p' is positioned outside of the patient's body, and the second expandable member 6412' can slide along an axial length of the tether 6416' in a compressed position. In this way, a user can selectively position the second expandable member 6412' relative to the first expandable member 6410' and relative to the anastomosis 6800, and the user can monitor this positioning using the scope 6418. After the second expandable member 6412' is in a desired position, the proximal terminal end 6416p' of the tether 6416' can be coupled to an inflation source (not shown) and can be activated to expand the second expandable member 6412', as shown in FIGS. 12D and 12E. The scope 6418 can be retracted proximally and removed from the patient's body. As a procedure is performed on the tubular body organ 6800, such as delivering sealant 6300 into the sealing cuff 6000 positioned around the anastomosis 6808, a volume of the expandable members 6010', 6012' can be adjusted as desired to ensure that the outer surface of the tubular body organ 6800 and the sealing cuff 6000 hold the sealant 6300 during the curing process. After the sealant 6300 has substantially cured to its solidified state, the first and second expandable members 6010', 6012' can be deflated to the compressed position and then retracted proximally and removed from the patient's body.

Methods for Testing a Seal of an Organ

Figure 13:
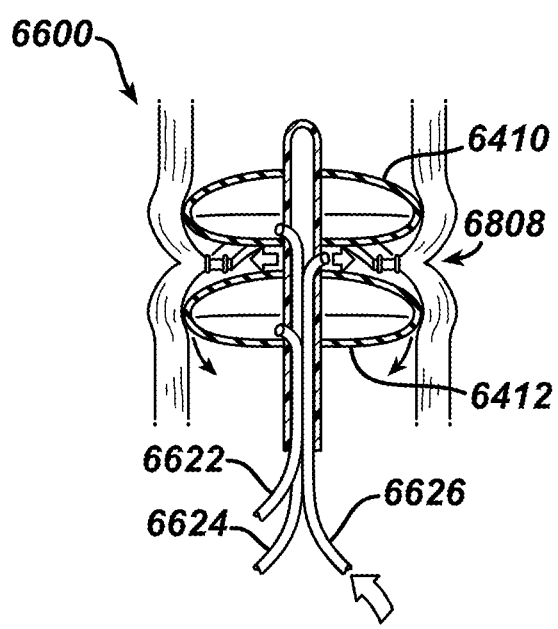
FIG. 13 is a cross-sectional view of a first and second expandable members forming a seal inside of the tubular organ and gas being delivered to the sealed space between the expandable members so as to test leakage from the anastomosis.

Methods for testing a seal of an anastomosis can improve a surgical outcome by providing feedback to a surgeon as to the effectiveness of a seal along an anastomosis. More specifically, this can allow a surgeon to intervene and correct any leaks prior to completing the procedure. A leak test can be performed before a sealant is applied to an anastomosis and if liquid or gas fails to leak out of the staple line of the anastomosis, a surgeon may determine that it is not necessary to apply a reinforcing sealant to the anastomosis. As another example, the leak test can be performed after the sealant is applied to allow a surgeon to confirm that the sealant has penetrated the staple line and cured to its solidified state. While any of the expandable members provided herein can be modified to include an additional lumen for delivering liquid or gas to the portion of the tubular body organ adjacent to the anastomosis, specific reference is made to the expandable device of FIG. 7 for performing a leak test. After fluid has been delivered to the device so that the expandable members 6410, 6412 are in their expanded position, as shown in FIG. 13, fluid or gas can be delivered to the third inflation lumen 6626. This fluid can be trapped between first and second expandable members 6410, 6412, thereby exerting pressure on the anastomosis 6808. With the expandable members 6410, 6412 so positioned, leaks are more likely to occur at the staple line due to stretching of the tissue. As the surgeon continues to deliver the liquid or gas to this portion of the anastomosis 6808 until a desired volume and pressure is achieved in the expandable members 6410, 6412, any leaks can be observed using known imaging techniques. For example, a surgeon can confirm the presence of leaks by visually identifying gas bubbles or liquid moving out of the tubular body organ 6800 through the staple line. As previously mentioned, the use of dyes or contrast material can assist a surgeon with visually identify these leaks. The method can further include delivering therapeutic agents through the tubular body organ 6800 and into the anastomosis 6808 using the inflation lumen 6626. Such therapeutic agents can include, by way of non-limiting example, additional sealant material, adhesives, coagulants, promoters of healing, oncologic medicines, and colonic stents. The method can be performed in other ways. For example, a fourth lumen (not shown) can also be provided in the expandable device 6600 and a surgeon can use this fourth lumen to drain gas or liquid from the space between the expandable members 6410, 6412, such as to allow the leak test to be performed multiple times and/or to deliver various therapeutic agents, gas, liquid, etc. to the anastomosis 6808.

Figure 14A:
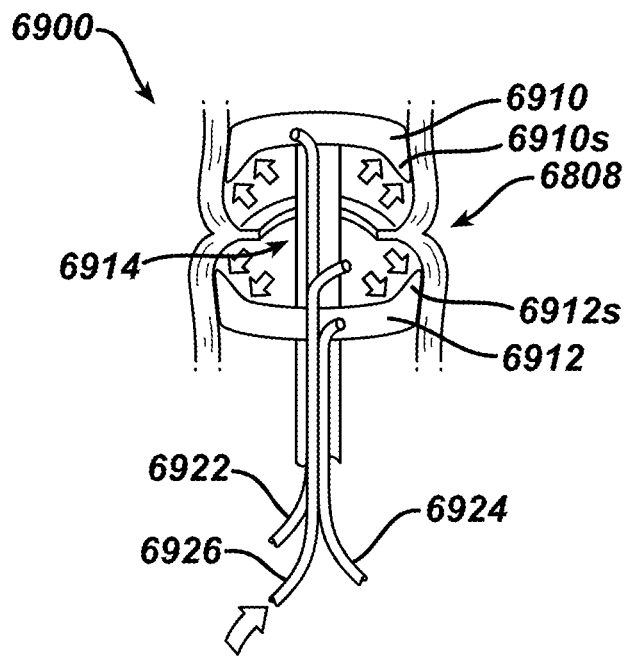
FIG. 14A is a cross-sectional view of another embodiment of first and second expandable members with gas delivered to a space therebetween so as to test leakage from the anastomosis.
Figure 14B:
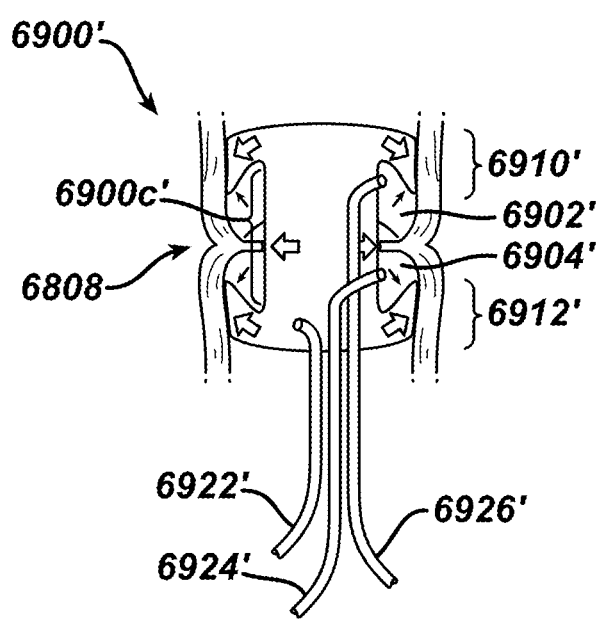
FIG. 14B is a cross-sectional view of an embodiment of an expandable member having a central portion configured to support the anastomosis as fluid is delivered to the space adjacent to the anastomosis so as to test leakage therefrom.

Other methods for performing a leak test are also shown in FIGS. 14A and 14B, which illustrate pressure being applied to the anastomosis 6808 at various locations. For example, FIG. 14A illustrates an expandable device 6900 having first and second mandrels 6910, 6912 having a thickness that increases from a central portion of the mandrels 6910, 6912 to an outer circumference thereof for facilitating a seal between the expandable device 6900 and the tubular body organ 6800. As shown, a side portion 6910s, 6912s of the mandrels 6910, 6912 can have an increased thickness near the inner wall of the tubular body organ 6800 so that a greater surface area of the expandable member 6910, 6912 contacts the inner surface of the organ 6800. In this way, the expandable device 6900 can withstand increased pressures and maintain in a substantially fixed position relative to the anastomosis 6808 as the fluid is delivered into a sealed space 6914 in between the first and second expandable mandrels 6910, 6912. As in the previous embodiment, the first expandable member 6910 can be inflated by delivering fluid thereto via a first inflation lumen 6922 and the second expandable member can be inflated by delivering fluid thereto via a second inflation lumen 6924 simultaneously or successively in any order. As shown in FIG. 14A, once the expandable mandrels 6910, 6912 are in the expanded positions, fluid such as gas can be delivered into the space 6914 between the mandrels 6910, 6912 via a third inflation lumen 6926. This can ensure that fluid does not leak out proximal or distal to the anastomosis 6808, as such leaking could decrease a pressure being applied to the anastomosis 6808 and thus, decrease an effectiveness of the leak test.

FIG. 14B illustrates a method for performing a leak test that includes a single expandable mandrel 6900' having proximal and distal portions 6912', 6910', sized and shaped similar to the expandable mandrels 6910, 6912 of FIG. 14A. Fluid can be delivered to the expandable mandrel 6900' via the first inflation lumen 6922' to expand the mandrel 6900'. In the expanded position, the expandable mandrel 6900' has an enlarged central portion 6900c' positioned adjacent to and in direct contact with the anastomosis 6800. The central portion 6900c' of the expandable mandrel 6900' can exert a force perpendicular to the anastomosis 6808 and forming a staple line support zone, as shown. In this way, the expandable mandrel 6900' can prevent the anastomosis 6808 from compressing radially inward as the sealant 6300 is curing therearound and held in position in the cuff 600. Radial compression of the staple line is undesirable because it could decrease a diameter of the tubular body organ 6800 and prevent liquids and solids from passing therethrough. When the expandable mandrel 6900' is so positioned, fluid can be delivered to a first chamber 6902' positioned distal to the anastomosis 6808 via a second inflation lumen 6924', the first chamber 6902' being positioned between the distal portion 6910' and the anastomosis 6808. Simultaneously or sequentially, fluid can be delivered to a second chamber 6904' positioned proximal to the anastomosis 6808 via a third inflation lumen 6926', the second chamber 6904' being positioned between the proximal portion 6912' and the anastomosis 6808. As in the previous embodiments, a surgeon can visually identify any leaks from the anastomosis 6808. If leaks are observed, a surgeon can apply sealant 6300 to the anastomosis using a sealing cuff 6000, etc. and perform the leak test any number of times until the surgeon determines that the leaks are repaired.

After the leak test is performed and/or where a sealant has been cured to reinforce the anastomosis, the liquid or gas can be removed from the expandable member so that the expandable member is in the compressed position and the expandable device can be retracted proximally and out of the patient's body.

Reprocessing

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument, which can include an adjunct material, is obtained and if necessary cleaned. The instrument can then be sterilized. In some embodiments, the instrument can be dried, e.g., in an oven, together with a desiccant item, which can have a greater affinity for moisture than the adjunct material. In one sterilization technique, the instrument is placed in a closed and sealed container, such as a plastic or TYVEK bag or a foil bag. The container and instrument are then placed in a field of radiation that can penetrate the container, such as gamma radiation, x-rays, or high-energy electrons. The radiation kills bacteria on the instrument and in the container. In another sterilization technique, the instrument is placed in a first container, such as a plastic or TYVEK bag, having a vapor permeable backing. The first container can then be packaged in a second container, e.g., a foil bag, which can be left open. The first and second containers, together with the instrument, can undergo ethylene oxide sterilization. The second container can then be sealed to prevent moisture exposure. Prior to sealing, a desiccant item may be included in at least one of the first and second containers to further prevent changes to one or more device components. In both techniques, the sterilized materials can then be stored in the sterile container(s) to keep the materials sterile until the container(s) is/are opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical kit, comprising:
   a liquid sealant configured to cure into a solidified state;
   a sealing cuff having a sidewall with first and second ends removably mated to one another to form an enclosed loop, the sidewall defining an interior chamber, the sealing cuff having a plurality of openings formed therein, and the sealing cuff being configured to be disposed around a body lumen such that the interior chamber is sealed between the sidewall and the body lumen to allow the liquid sealant to be received therein and to directly contact the body lumen; and
   a suture extending along an inner surface of the sealing cuff and passing through each of the plurality of openings, the suture being configured to be detached from the sealing cuff after the sealant has cured into the solidified state and thereby release the sealant in the solidified state from the sealing cuff.

2. The kit of claim 1, wherein the sealing cuff has a passageway extending circumferentially therearound in which the suture is positioned, the plurality of openings being in communication with the passageway.

3. The kit of claim 1, wherein the sealing cuff has a passageway extending circumferentially therearound, the suture extending through the passageway.

4. The kit of claim 3, wherein the suture includes a first suture extending through the passageway and a second suture disposed in a criss-cross pattern on the inner surface of the sealing cuff.

5. The kit of claim 1, wherein the sealing cuff has a plurality of protrusions formed on the inner surface of the sealing cuff, the plurality of protrusions being configured to facilitate distribution of the sealant within the interior chamber.

6. The kit of claim 1, wherein the plurality of protrusions are spaced evenly about a circumference of the sidewall.

7. The kit of claim 1 wherein the sidewall is substantially hemi-spherical and the inner surface of the sealing cuff is substantially concave.

8. The kit of claim 1, further comprising at least one expandable member configured to move from a compressed position to an expanded position and having a shape that substantially corresponds to a shape of the interior chamber of the sealing cuff when the at least one expandable member is in the expanded position.

9. The kit of claim 1, wherein the sealant is selected from the group consisting of fibrin, thrombin, a hydrogel, benzocaine, cyanoacrylate, polyglycolic acid, hyaluronic acid, magnesium peroxide, hydrogen peroxide, platelet rich plasma, and combinations thereof.

10. The kit of claim 1, wherein the sealant is configured to transition from the liquid to the solidified state after a predetermined amount of time.

11. A surgical kit, comprising:
    a liquid sealant configured to cure into a solidified state;
    a sealing cuff having a sidewall with first and second ends removably mated to one another to form an enclosed loop, the sidewall defining an interior chamber, the sealing cuff having a passageway extending circumferentially therearound, and the sealing cuff being configured to be disposed around a body lumen such that the interior chamber is sealed between the sidewall and the body lumen to allow the liquid sealant to be received therein and to directly contact the body lumen; and
    a suture extending along an inner surface of the sealing cuff and extending through the passageway, the suture being configured to be detached from the sealing cuff after the sealant has cured into the solidified state and thereby release the sealant in the solidified state from the sealing cuff.

12. The kit of claim 11, wherein the suture includes a first suture extending through the passageway and a second suture disposed in a criss-cross pattern on the inner surface of the sealing cuff.

13. The kit of claim 11, wherein the sidewall is substantially hemi-spherical and an inner surface of the sealing cuff is substantially concave.

14. The kit of claim 11, wherein the sealing cuff has a plurality of extensions configured to distribute the sealant within the interior chamber, the plurality of extensions being sized and shaped such that when the sealing cuff is disposed around a tubular body organ, the plurality of extensions contact an outer surface of the tubular body organ.

15. The kit of claim 14, wherein the plurality of extensions are spaced evenly about a circumference of the sidewall.

* * * * *